(12) United States Patent
Kim et al.

(10) Patent No.: US 12,264,305 B2
(45) Date of Patent: Apr. 1, 2025

(54) DEVICES AND METHODS FOR ISOLATING A MIGRATORY CELL POPULATION

(71) Applicants: Board of Regents, The University of Texas System, Austin, TX (US); THE BOARD OF REGENTS OF THE UNIVERSITY OF OKLAHOMA, Norman, OK (US)

(72) Inventors: Young-tae Kim, Arlington, TX (US); Loan Bui, Arlington, TX (US); James Battiste, Edmond, OK (US); Xue Cai, Edmond, OK (US); Michael Sughrue, Sydney (AU)

(73) Assignees: BOARD OF REGENTS, THE UNIVERSITY OF TEXAS SYSTEM, Austin, TX (US); THE BOARD OF REGENTS OF THE UNIVERSITY OF OKLAHOMA, Norman, OK (US)

( * ) Notice: Subject to any disclaimer, the term of this patent is extended or adjusted under 35 U.S.C. 154(b) by 686 days.

(21) Appl. No.: 16/574,587

(22) Filed: Sep. 18, 2019

(65) Prior Publication Data

US 2020/0087606 A1 Mar. 19, 2020

Related U.S. Application Data

(60) Provisional application No. 62/732,806, filed on Sep. 18, 2018.

(51) Int. Cl.
| | |
|---|---|
| C12M 3/06 | (2006.01) |
| C12M 1/00 | (2006.01) |
| C12M 1/26 | (2006.01) |
| C12N 5/09 | (2010.01) |

(52) U.S. Cl.
CPC ............ *C12M 23/16* (2013.01); *C12M 29/04* (2013.01); *C12M 33/00* (2013.01); *C12N 5/0693* (2013.01)

(58) Field of Classification Search
CPC ...... C12M 23/16; C12M 29/04; C12M 33/00; C12M 47/04; C12N 5/0693
See application file for complete search history.

(56) References Cited

PUBLICATIONS

Chen et al. Single-cell Migration Chip for Chemotaxis-based Microfluidic Selection of Heterogeneous Cell Populations. Scientific Reports (2015). 5(09980), 13 pages. (Year: 2015).*

Liu et al. A Microfluidic Device for Blood Cell Sorting and Morphology Analysis. 17th International Conference on Miniaturized Systems for Chemistry and Life Sciences (2013), 1003-1005 (Year: 2013).*

(Continued)

*Primary Examiner* — Sean C. Barron
(74) *Attorney, Agent, or Firm* — Maynard Nexsen PC; John P. Zimmer

(57) ABSTRACT

A method and device for isolating a migratory cell population from a mixed population of migratory cells and non-migratory cells is described herein. The method comprises placing the mixed population of migratory cells and non-migratory cells in contact with a device having one or more microchannels; and isolating the migratory cell population within the microchannels following an incubation period, wherein the one or more microchannels have an average size in a proliferation direction of the migratory cells that is less than a minimum proliferation space of the migratory cells along the proliferation direction.

17 Claims, 21 Drawing Sheets

(56) References Cited

PUBLICATIONS

Invitrogen technical manual B-084243 0110 ("Cell Culture Basics") (2010), 56 pages. (Year: 2010).*

Baghat et al. Pinched flow coupled shear-modulated inertial microfluidics for high-throughput rare blood cell separation. Lab on a Chip (2011), 11, 1870-1878. (Year: 2011).*

Dean L. Blood Groups and Red Cell Antigens [Internet]. Bethesda (MD): National Center for Biotechnology Information (US); 2005. Chapter 1, Blood and the cells it contains. Available from: https://www.ncbi.nlm.nih.gov/books/NBK2263/ (Year: 2005).*

Mcfaul et al. Cell separation based on size and deformability using microfluidic funnel ratchets. Lab on a Chip (2012), 12, 2369-2376. (Year: 2012).*

Meyer et al. Multi-depth valved microfluidics for biofilm segmentation. J. Micromech. Microeng. 25 (2015) 095003. (Year: 2015).*

Friedl et al., "Nuclear mechanics during cell migration", Curr Opin Cell Biol., 23(1), 2011, pp. 55-64.

Ridley et al., "Cell Migration: Integrating Signals from Front to Back", Science, vol. 302, Issue 5651, 2003, pp. 1704-1709.

* cited by examiner

Seeding Reservoirs

| Seeding mixed cells and culturing for 4-7 days to allow Migratory cells to migrate toward microchannels | Removing non-migratory cells and peeling off microchannel array | Migrating cells are present in both peeled microchannel array and well-plate where microchannel array was placed | Migrating cells are collected from both peeled microchannel array and area of well-plate where microchannel array was placed | Isolating Proteins |

FIG. 11

DEVICES AND METHODS FOR ISOLATING A MIGRATORY CELL POPULATION

CROSS-REFERENCE TO RELATED APPLICATIONS

This application claims priority under 35 U.S.C. § 119 to U.S. Provisional Patent Application No. 62/732,806, filed Sep. 18, 2018, the entirety of which is incorporated by reference herein.

STATEMENT REGARDING GOVERNMENT FUNDING

This invention was made with government support under grant no. RP150711 awarded by the Cancer Prevention and Research Institute of Texas (CPRIT. The government has certain rights in the invention.

FIELD

The invention is generally related to devices and methods for isolating a migratory cell population, and, more specifically, devices and methods for isolation of a migratory cell population from a mixed population of migratory and non-migratory cells.

BACKGROUND

The incidence of premature death in the United States is the second highest among cancer patients. More than 1.5 million new cases of cancer and approximately 600,000 deaths were estimated in 2016. Among these, cancer metastasis is a leading cause of death due to cells escaping from the primary tumor and invading distant sites. Few cases of metastatic cancers are found to be treatable and are rarely cured. However, cell migration is not only limited to cancer metastasis and progression, it is found to drive other diseases, including arthritis, atherosclerosis, mental retardation, and others. Cell migration is also a crucial step in embryonic development, wound healing, and tissue regeneration. Thus, there are increasing needs to research the migrating capabilities of cells to better understand the molecular mechanisms that enable and promote cell migration, as well as formulate treatment regimens to target aberrantly migrating cells.

In most in vitro research studies, cells are cultured on traditional cell culture dishes and subjected to various challenges, such as chemotherapy, radiation, or a scratch for migration, followed by collection for analysis. However, a major drawback to this approach is that results are derived from both proliferating/non-migrating cells and migrating cells. An analysis of this dual population may confound results making it difficult to distinguish and exclusively, study the migrating cells.

There are several conventional experimental methods that attempt to examine the therapeutic effects of target molecules on migrating cells. For example, three-dimensional cell culture has become a popular method that allows examination of both migration and invasion, and is believed to more closely mimic the natural environment of the cells. Although methods such as three-dimensional cell culturing enable the study of active migration, these methods are not suitable for well-established analytical methods that require large amounts of cells, such as Western blots. Moreover, due to the often limited amount of harvested material, these methods are limited in scope and quantity of experimental analyses that can be conducted, such as DNA, RNA, lipid, and/or protein analysis. As cell migration is a biological phenomenon found in normal physiology and aberrant pathologies, such as cancer, atherosclerosis and others, improved methods of isolating migratory cells for molecular analysis is needed to better understand the molecular mechanisms of cell migration and to develop efficient therapeutic regimens against different types of disease.

SUMMARY

In one aspect, methods of isolating a migratory cell population from a mixed population of migratory cells and non-migratory cells are described herein. In some embodiments, these methods provide one or more advantages over other methods. For example, the methods described herein can be used to isolate a population of migratory cells from a mixed population of both migratory cells and non-migratory cells, rendering a more "pure" sampling of migratory cells. In some embodiments, the methods can render a population of migratory cells sufficient to perform one or more types of molecular analysis, and in some instances, in two, three, or more than three replicates. The methods described herein can integrate with well-known and widely used cell culture equipment and techniques, including standard cell culture dishes and molecular analysis protocols, such as Western Blot, immunohistochemistry, qPCR, and others.

In some embodiments, a method of isolating a migratory cell population from a mixed population of migratory cells and iron-migratory cells comprises placing the mixed population of migratory cells and non-migratory cells in contact with one or more microchannels, and isolating the migratory cell population within the microchannels following an incubation period. The method, in some embodiments, further comprises collecting the migratory cell population from the microchannels. The one or more microchannels, in some embodiments, have an average size in a proliferation direction of the migratory cells that is less than a minimum proliferation space of the migratory cells along the proliferation direction. In some instances, the proliferation direction is a horizontal direction and the mixed population of cells are eukaryotic cells. In other instances, the proliferation direction is a vertical direction and the mixed population of cells are microbial cells. In some embodiments, the mixed population is placed in contact with a plurality of microchannels, and the microchannels comprise an array. Furthermore, in some instances, at least 500 migratory cells are isolated within the microchannels.

In some embodiments, placing the mixed population of migratory cells and non-migratory cells in contact with one or more microchannels comprises seeding the mixed population proximate an opening to the one or more microchannels. In other embodiments, placing the mixed population of migratory cells and non-migratory cells in contact with one or more microchannels comprises placing the one or more microchannels adjacent to seeded cells of the mixed population.

In some embodiments, isolating the migratory cells within the microchannels comprises removing the non-migratory cells from contact with the microchannels and/or removing the microchannels from a cell culture.

In some embodiments, collecting the migratory cell population from the microchannels comprises extracting the migratory cell population from inside the microchannels. In some instances, collecting the migratory cell population from the microchannels comprises exposing the migratory cell population to a protease enzyme, for example, trypsin.

In some embodiments, the microchannels of the method described herein are disposed in a cell culture. The average width of the one or more microchannels, in some embodiments, is less titan 10 μm to prevent cell proliferation within the microchannels, resulting in the exclusive migrating cells within the microchannels. The microchannels, in some instances, are open on a side, whereas in other instances, the microchannels comprise a longitudinally extending receiving space formed by four connected sidewalls. In some embodiments, the microchannels are free of a chemoattractant chemical or concentration gradient having a purpose of inducing, encouraging, or guiding migration of the cells. Additional features of the microchannels can include, but are not limited to, openings on an end that are permeable to a liquid media via capillary action along the length of the microchannels, walls that are impermeable to the migratory and non-migratory cells, walls formed from a polymer, and/or walls formed from a polysiloxane.

In another aspect, a device for isolating migratory cells from a mixed population of migratory cells and non-migratory cells having one or more microchannels is described herein. In some embodiments, the device further comprises a cell culture and the microchannels are disposed in the cell culture. A device having two or more microchannels, and in some embodiments, the two or more microchannels comprise an array. The microchannels, in some embodiments, have an average size in a proliferation direction of the migratory cells that is less than a minimum proliferation space of the migratory cells along the proliferation direction. In some embodiments, the microchannels are open on a side, whereas in other embodiments the microchannels are enclosed, having a longitudinally extending cell receiving space formed by four connected sidewalls. The one or more microchannels, in some instances, have an average width of less than 10 μm. In some cases, the one or more microchannels have a total internal volume equal to or greater than the volume of at least 500 migratory cells. In some embodiments, the one or more microchannels are permeable to a liquid media. In other embodiments, the one or more microchannels have sidewalk formed from a polymer. For example, in some instances, the polymer-based sidewalls are impenetrable to the migratory cells. In other embodiments, the microchannels are coated. For example, a coating may comprise any chemical substance, such as a small molecule compound or composition comprising an active ingredient.

In another aspect, a method of performing molecular analysis is described herein. The method, in some embodiments, comprises isolating a population of migratory cells from a mixed population of migratory and non-migratory cells and performing a molecular analysis on the population of migratory cells. In some embodiments, the population of migratory cells includes at least 500 cells. Additionally, isolating a population of migratory cells can comprise placing the mixed population of migratory cells and non-migratory cells in contact with one or more microchannels and collecting the migratory cell population from the microchannels following an incubation period. In some instances, the one or more microchannels have an average size in a proliferation direction of the migratory cells that is less than a minimum proliferation space of the migratory cells along the proliferation direction. The proliferation direction can be horizontal and the mixed population of cells can be eukaryotic cells. In other instances, the proliferation direction can be vertical and the mixed population of cells can be microbial cells. In some embodiments, the method described herein comprises a molecular analysis that includes, but is not limited to, one or more of a proteomic analysis, a metabolomic analysis, a transcriptomic analysis, and/or a genomic analysis.

These and other embodiments are described in greater detail in the following detailed description.

BRIEF DESCRIPTION OF THE DRAWINGS

The invention will now be described by way of example, with reference to the accompanying figures.

FIG. 11 is a pictorial timeline of separating migratory cells from non-migratory cells using a microchannel device, and isolating proteins in the separated migratory cells.

DETAILED DESCRIPTION

Figure 1A:
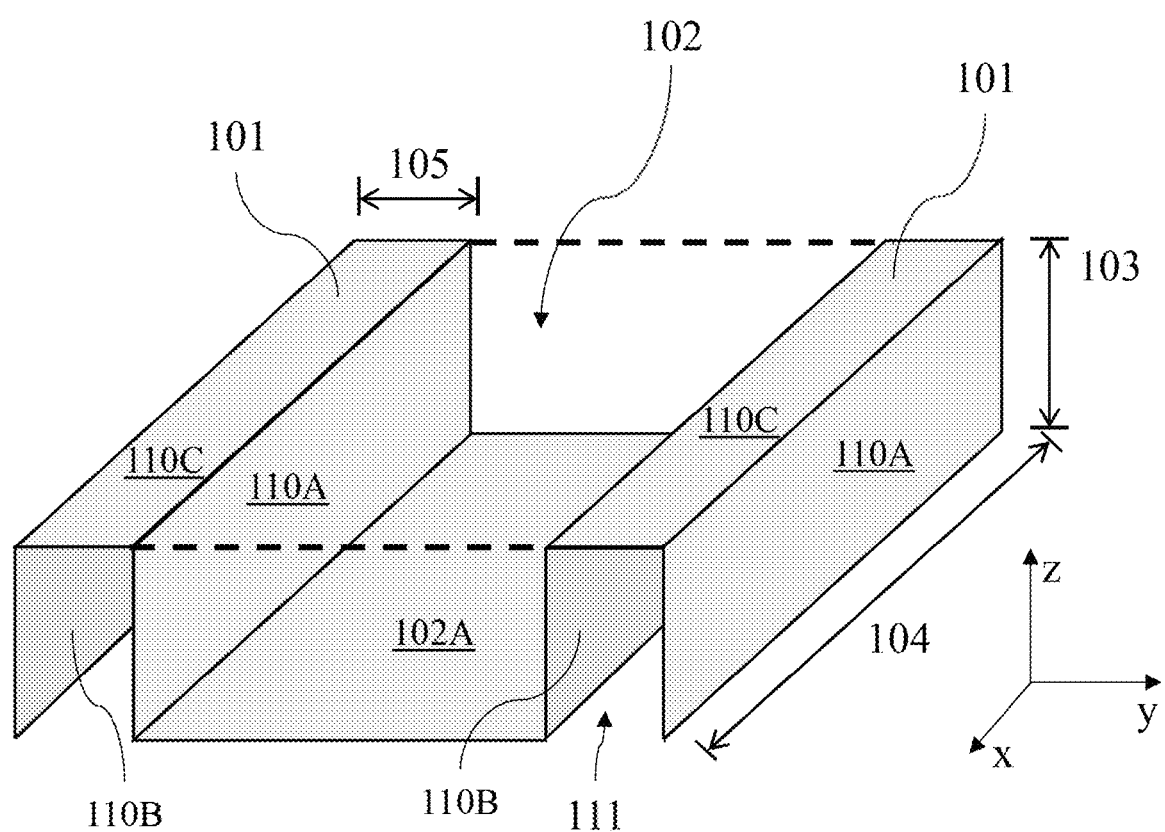
FIG. 1A is a perspective view of an array of microchannels.

Embodiments described herein can be understood more readily by reference to the following detailed description and examples. Methods, devices, and features described herein, however, are not limited to the specific embodiments presented in the detailed description and examples. It should be recognized that these embodiments are merely illustrative of the principles of this disclosure. Numerous modifications and adaptations will be readily apparent to those of skill in the art without departing from the spirit and scope of the disclosure.

In addition, all ranges disclosed herein are to be understood to encompass any and all subranges subsumed therein. For example, a stated range of "1.0 to 10.0" should be considered to include any and all subranges beginning with a minimum value of 1.0 and ending with a maximum value of 10.0 or less, e.g. 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the endpoints 5 and 10.

Further, when the phrase "up to" is used in connection with an amount or quantity, it is to be understood that the amount is at least a detectable amount or quantity. For example a material present in an amount "up to" a specified amount can be present from a detectable amount and up to and including the specified amount.

I. Devices for Isolating a Migratory Cell Population

In one aspect, devices for isolating a migratory cell population are described herein. In some embodiments, a device comprises one or more microchannels having an average size in a proliferation direction of the migratory cells that is less than a minimum proliferation space of the migratory cells along the proliferation direction.

The one or more microchannels 101, as shown in FIG. 1, of a device described herein has a measureable length 104, width 105, and height 103. The length 104, width 105, and height 103 of the one or more microchannels 101 are each specific, measureable dimensions. As shown in FIG. 1A and FIG. 1B, the height 103 of the one or more microchannels 101 is a dimension corresponding to a z-directional axis relative to the pull of gravity. The length 104 corresponds to an x-directional axis, down which the migratory cells can migrate through the microchannels 101. The width 105 of the one or more microchannels 101 is measured along a y-directional axis orthogonal to both the length 104 and the height 103, and corresponds to a direction spanning across a parallel arrangement of two or more microchannels 101 positioned side-by-side. The width 105 and height 103 of a microchannel 101, together, represent a 2-dimensional cross-section of the microchannel 101 when viewed along the length 104 of the microchannel 101 (e.g., along the x-directional axis). Each microchannel 101 has at least one opening 106 on one end of the length 104.

Each microchannel 101 has a length 104 greater than a width 105. For example, in some embodiments, the length 104 of one microchannel 101 is about 100 to 10,000 times the width 105 of the microchannel 101. In other embodiments, the length 104 of each microchannel 101 is about 300 to 1500 times, about 600 to 1200 times, about 1000 times, at least 500 times, at least 600 times, at least 700 times, at least 800 times or at least 1000 times the width 105 of the same microchannel 101.

Each microchannel 101 is formed from a plurality of walls. As seen for example in FIG. 1A, each microchannel 101 can comprise a first and second sidewall 110A, 110B extending longitudinally along the x-directional axis. In an embodiment, the first and second sidewalls 110A, 110B are positioned approximately parallel along the x-directional axis. Each of the first and second sidewalls 110A, 110B can be approximately equal in length and height, generally having a length equal to length 104 and a height equal to, height 103, although in other instances the first and second sidewalk 110A, 110B can have different lengths and heights from each other. Each of the first and second sidewalls 110A, 110B has a first edge and art opposite second edge extending lengthwise along each of the first and second sidewalls 110A, 110B. A first connecting sidewall 110C extends from the first edge of the first sidewall 110A to a corresponding first edge of the second sidewall 110B. The first connecting sidewall 110C in some embodiments has, a length approximately equal to the length of the first and second sidewalk 110A, 110B, such as a length equal to length 104. The first connecting sidewall 110C has a width equal to width 105. Taken together, the first and second sidewalk 110A, 110B and the first connecting sidewall 110C form an approximate U-shape when viewed along the x-directional axis (i.e. longitudinally, along, the length 104). However, shapes known to the skilled artisan other than a U-shape are also contemplated. In some embodiments, each microchannel 101 is open on along the second edge of the first and second sidewalls 110A, 110B, such that the microchannel 101 is "open" or "open-topped". In other embodiments, each microchannel 101 further comprises a second connecting sidewall (not shown) extending from the second edge of the first sidewall 110A to the corresponding second edge of the second sidewall 110B to form a square of rectangular tube-like structure. The second connecting sidewall in some embodiments has a length approximately equal to the length of the first and second sidewalls 110A, 110B, such as a length equal to length 104. In some embodiments, the second connecting sidewall has a length equal to a length of the first connecting sidewall 110C. The second connecting sidewall has a width equal to width 105. In some embodiments, the second connecting sidewall has a width equal to a width of the first connecting sidewall 110C, although in other instances, the second connecting sidewall can have a width that is different than a width of the first connecting sidewall 110C. Taken together, the first and second sidewalk 110A, 110B, the first connecting sidewall 110C, and the second connecting sidewall form an approximate square, rectangular, or O-shape when viewed along the x-directional axis (i.e. longitudinally, along the length 104). Microchannels 101 having both the first connecting sidewall 110C and the second connecting sidewall are hence limited to height 103 by the first and second connecting sidewalls, exemplary second connecting sidewall 110D is shown in FIG. 1D. In embodiments having the second connecting sidewall, the microchannels 101 comprise a centrally-located, longitudinally extending cell receiving space formed by four connected sidewalls. In some instances, the microchannel 101 can be circular, oval, hexagonal, pentagonal, triangular, or any other shape not inconsistent with the objectives of this disclosure when viewed along the x-directional axis.

Each microchannel 101 can have one or more openings 111, where each opening 111 is positioned on an end of the microchannel, as shown for example in FIG. 1A.

Each microchannel 101 comprises an internally located cell receiving space (not specifically labeled but generally indicated by the arrow for the openings 111) extending longitudinally along the length of the microchannel 101 (along the z-directional axis). The cell receiving space is defined as the space between the first and second sidewalk 110A, 110B, and has a height approximately equal to the height 103 of the first and/or second sidewalls 110A, 110B. The cell receiving space has a width approximately equal to the width 105 of the first connecting sidewall 110C. The cell receiving space is in fluid communication with the opening 111, such that fluids and cells can pass through the opening 111 and enter the cell receiving space.

Figure 1B:
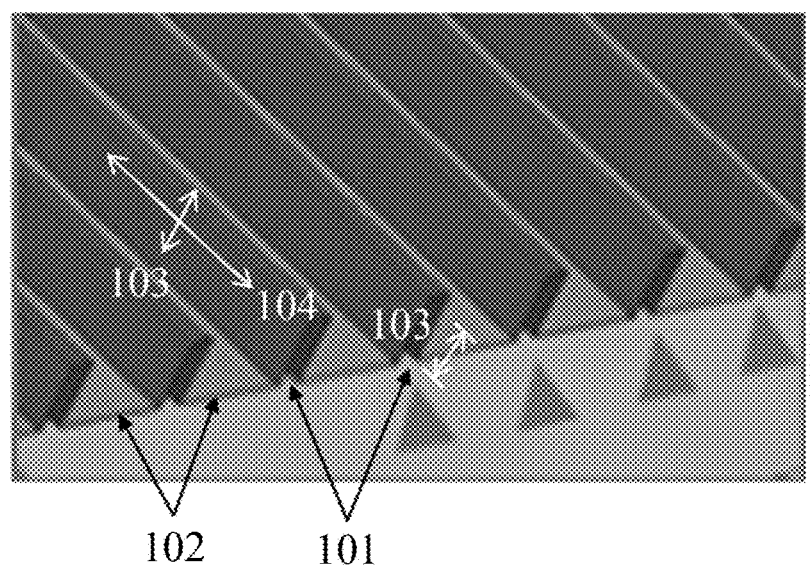
FIG. 1B is an expanded perspective view of a microchannel array having a plurality of parallel microchannels.
Figure 1C:
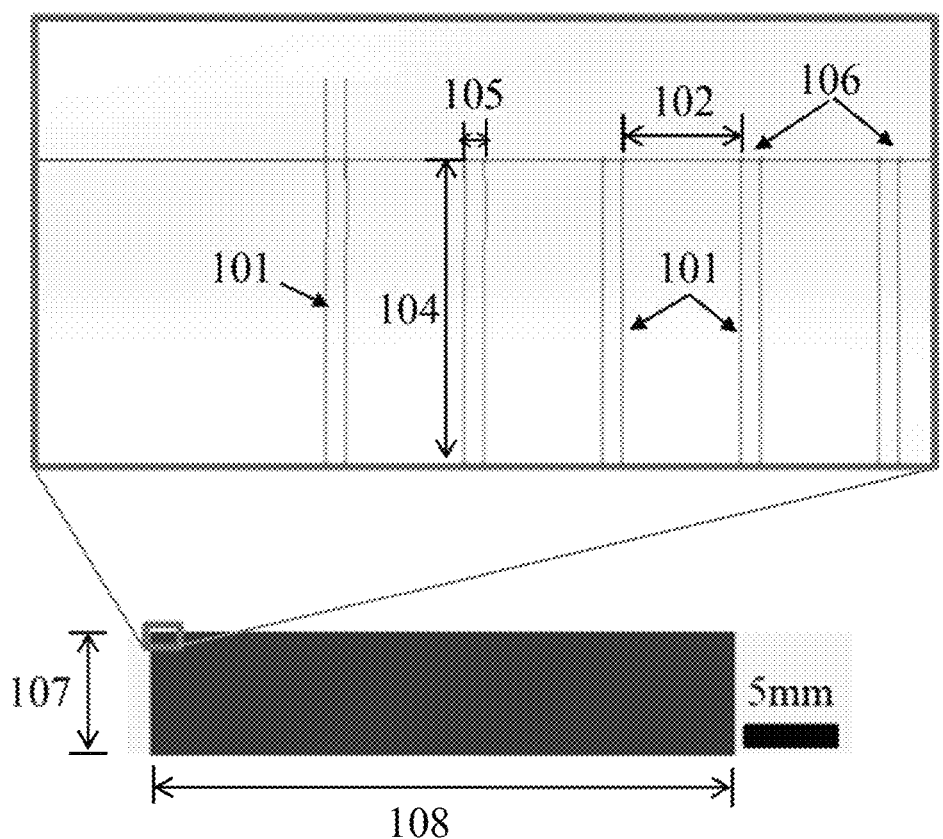
FIG. 1C is an expanded view of microchannels separated by a gap.
Figure 1D:
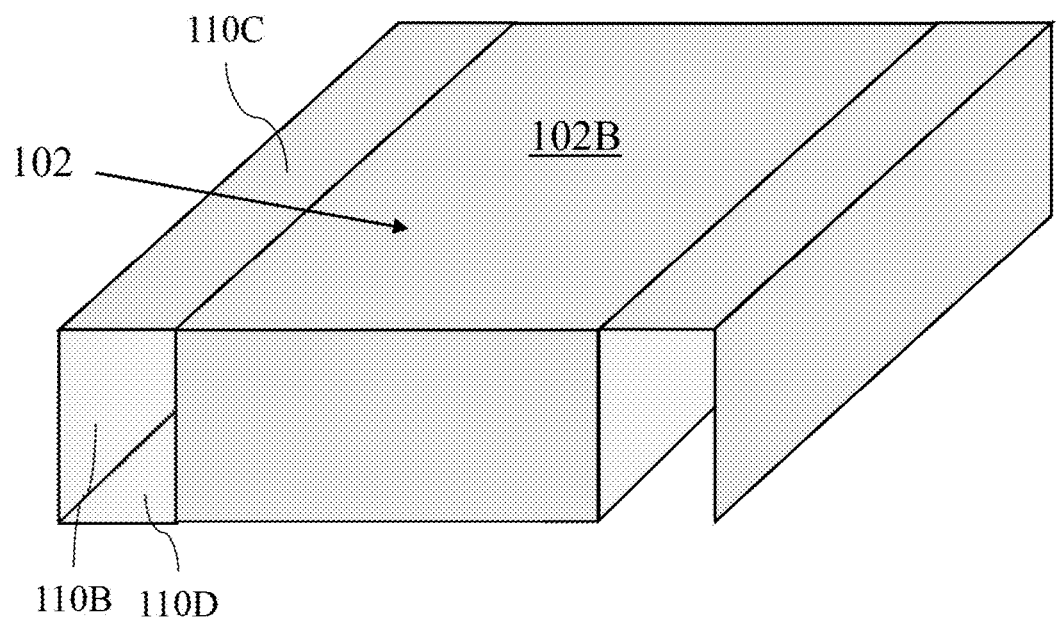
FIG. 1D is a perspective view of microchannels separated by a gap.

In some embodiments, two or more of the microchannels 101 are positioned together to form in an array, as shown in FIGS. 1A-1D. In some cases, an array of microchannels 101 comprises a plurality of microchannels, such as at least 300, at least 400, at least 500, at least 600, at least 700, or at least 800 microchannels, as generally shown in FIG. 1B. The array, in some embodiments is non-linear, wherein the two or more microchannels 101 are arranged in a non-parallel pattern, such as radial pattern. In other cases, and as shown in FIGS. 1A-1D, the array is linear, wherein the plurality of microchannels 101 are arranged in a substantially parallel pattern. For example, a linear array, as shown in FIG. 1C, comprises a plurality of microchannels 101 substantially parallel to one another.

In some embodiments, the one or more of microchannels 101 are substantially parallel and are separated by a gap 102. Gap 102 can be an empty volumetric space, as shown in FIG. 1A, wherein a width of the gap 102 is defined by the first and second sidewalls 110A, 110B of each neighboring or adjacent microchannel 101. For example, in some embodiments, the microchannels 101 do not share a sidewall, but instead each microchannel 101 stands independently of each other, as seen in FIG. 1A and FIG. 1B. Microchannels 101 that stand independently or alone can still be interconnected by at least one or more walls of the gap 102, such as a base wall 102A or barrier, thereby creating a uniform array. Thus, in some embodiments, the gap 102 is defined by at least three walls, wherein the first wall is shared with a first adjacent microchannel 101 (e.g. second sidewall 110B in FIG. 1A), the second wall is shared with a second adjacent microchannel 101 (e.g., first sidewall 110A in FIG. 1A), and the third wall interconnects the first and second walls at a substantially 90 degree angle (e.g., base wall 102A). The 90 degree angle is merely illustrative of one embodiment and should not be interpreted as limiting. In other instances, the third wall interconnects the first and second walls at other angles. The walls defining the gap 102 function as a cell barrier to prevent cells from migrating from the microchannel 101 into the gap 102.

Alternatively, in other embodiments the gap 102 can be an enclosed volumetric space, such as shown in FIG. 1D. In these embodiments, the gap 102 is defined by four, five, or six walls, as in FIG. 1D. A gap 102 that is enclosed can be either hollow or solid. A solid gap 102 can also represent a solid wall 102B that is shared by adjacent microchannels 101. Thus, in some cases, the microchannels 101 can share a wall. The shared wall 102B can have a variable thickness that is defined as the width of the gap 102. The shared wall 102B can be hollow or solid, or in some cases can be partially hollow or partially solid. A gap 102 defining and enclosed volumetric space or a shared wall 102B can further have a height that is substantially the same or substantially different than the height 103 of the microchannels 101.

As the one or more microchannels 101 have a defined length 104, width 105, and height 103, so does a linear array of microchannels 101, as shown in FIG. 1C. The total length 107 of the linear array corresponds to the length 104 of the microchannels 101 in some instances. Therefore, the total length 107 of the linear array and the length 104 of the microchannels 101 can substantially be the same, although the total length 107 and the length 104 can be different in other embodiments. The total height of the linear array can correspond to the height 103 of the microchannels 101, and therefore, can also substantially the same, although the total height of the linear array can be different in other embodiments. The total width 108 of the linear array is measured along the same axis (i.e., along the y-directional axis) as the width 105 of the microchannels 101. However, the total width 108 of the linear array is the sum of the width 105 of each microchannel 101 plus the width of each gap 102 separating the two or more microchannels 101 in the array.

Figure 3:
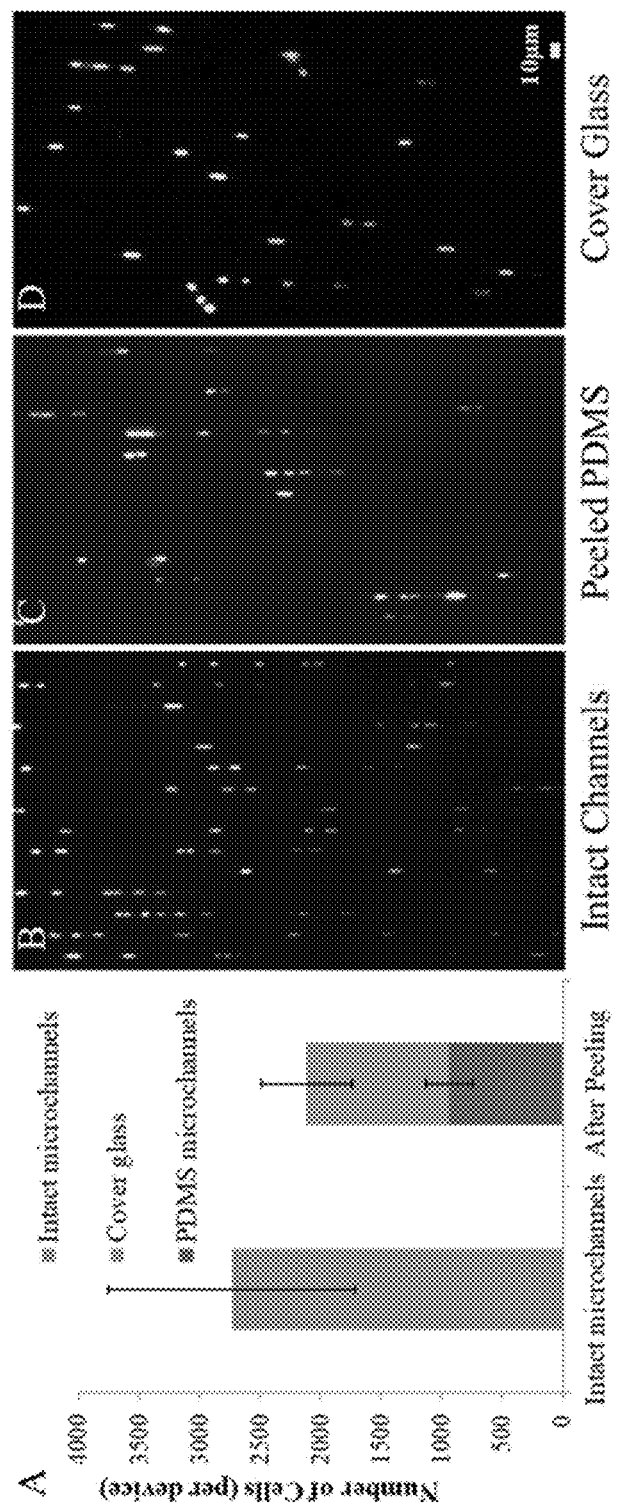
FIG. 3 illustrates quantification and immunofluorescent staining of migratory cells within microchannels.
Figure 4:
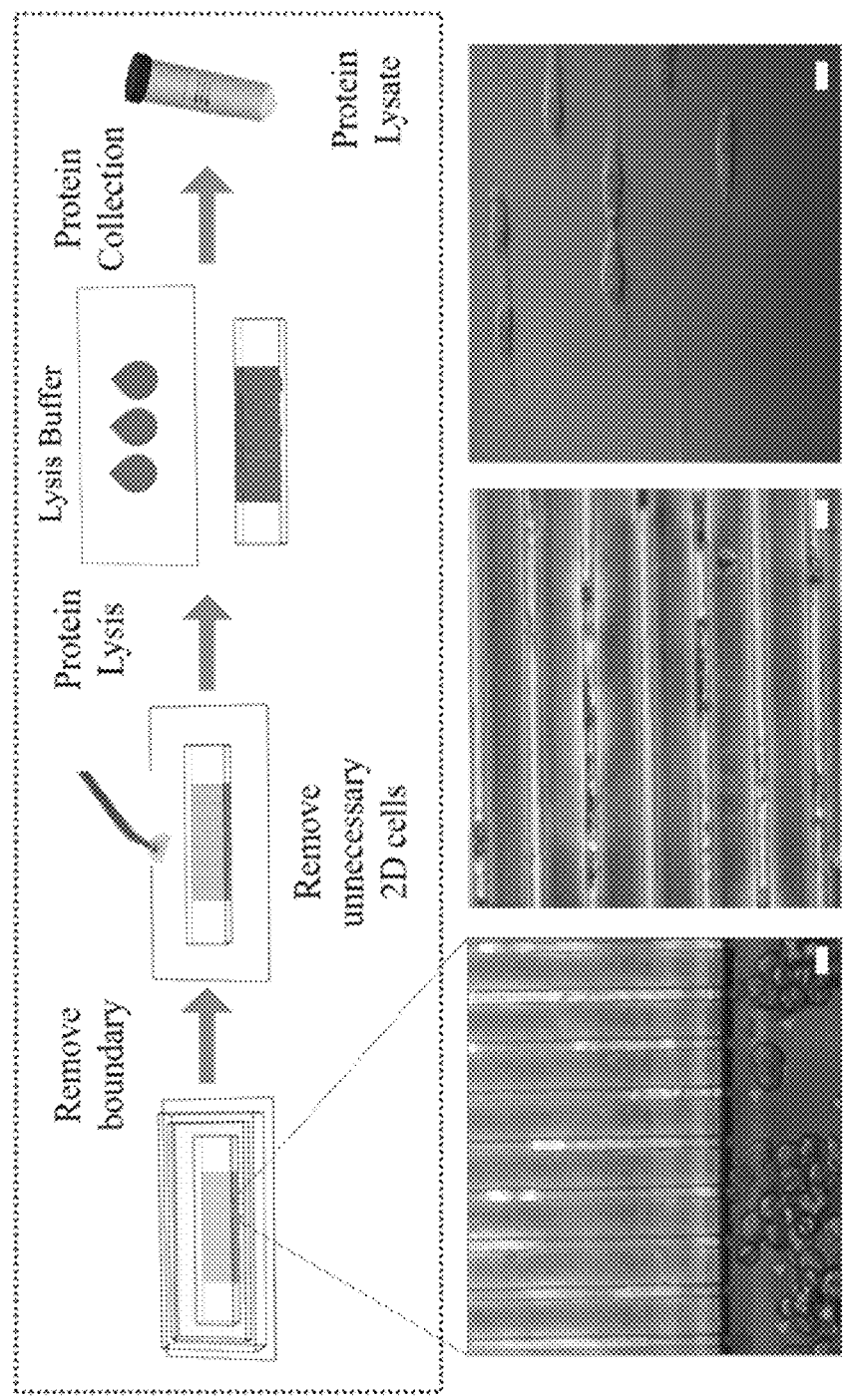
FIG. 4 shows a process of collecting protein from migratory cells isolated within microchannels with corresponding microscopy photographs of the microchannels.
Figure 7:
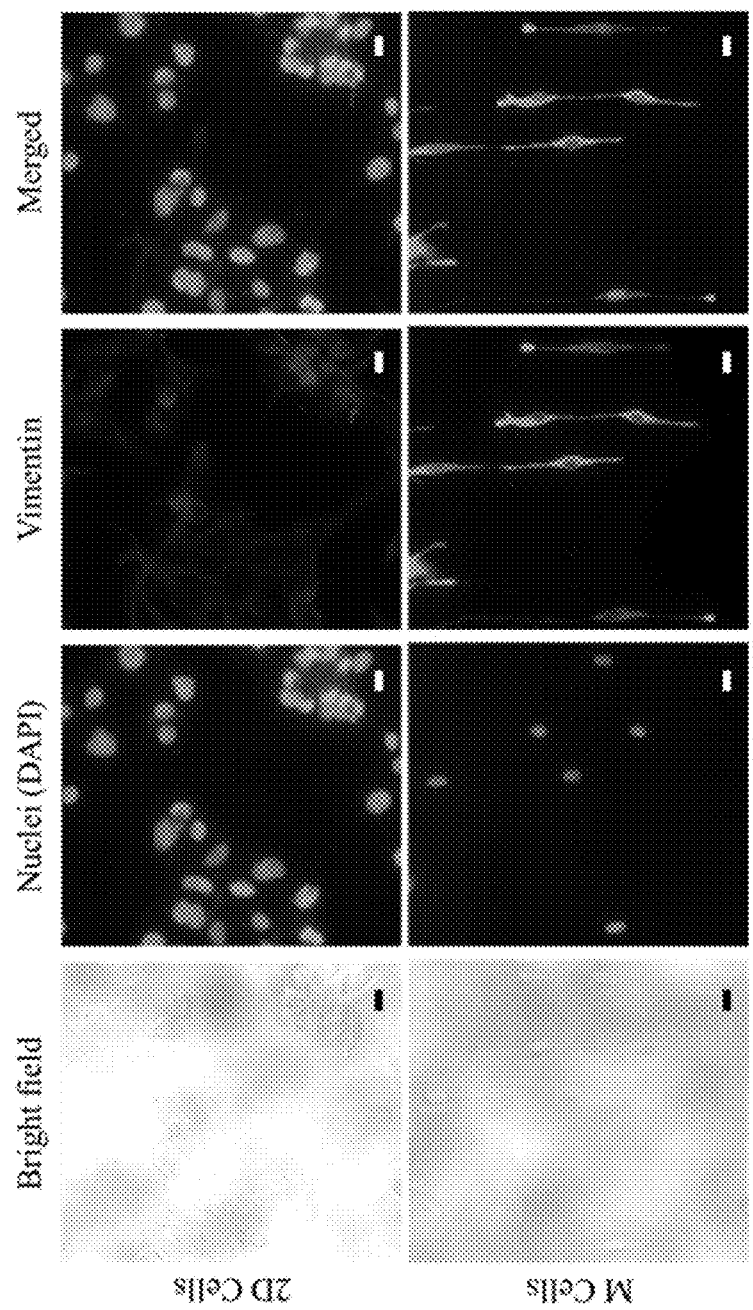
FIG. 7 shows photographic views of migratory and non-migratory cells stained with molecular markers.

The configuration of the array, including its overall shape and dimensions, in some embodiments, allows visual tracking of individual migratory cells within the microchannels 101, as shown in FIG. 3, FIG. 4, and FIG. 7. In some cases, visual tracking of the migratory cells within the microchannels 101 is performed using a marker, such as one or more fluorescent markers or other dyes. The marker can be visible either with or without a microscope. The visible resolution of single migratory cells within the array is, at least in part, determined by the dimensions of microchannels 101 and the gaps 102. For example, the thickness or width of the gap 102 should be large enough to discern a single migratory cell within one microchannel 101 from a different single migratory cell within an adjacent microchannel 101, even with moderate over exposure. In some cases, the gap 102 can be substantially equal to or greater than the size of the migrating cell or the soma of the migrating cell. In some embodiments, the gap 102 is at least 5 µm, at least 10 µm, at least 15 µm, at least 20 µm, at least 25 µm, at least 30 µm, at least 35 µm, at least 40 µm, at least 45 µm, at least 50 µm, or at least 60 µm.

A proliferation direction, in some embodiments, is a direction along a plane in which a cell attached to a surface of the plane requires space to grow and/or enter a proliferative stage of the cell cycle. In some instances, a proliferation direction is a substantially horizontal direction, corresponding to an x-y-plane, in which cells attached to a surface of the x-y-plane require sufficient space to grow in preparation for cell division. In other embodiments, a proliferation direction is a non-horizontal direction, or a substantially vertical direction (z-direction), in which cells that proliferate in a colony require sufficient space to grow in preparation for cell division.

A minimum proliferation space, in some embodiments, is the minimum amount of space required for a cell to enter a proliferative state and/or transition from a migratory state to a proliferative state. Entering a proliferative state can require a cell to morphologically change and/or increase in size. Thus, a minimum proliferation space, in some embodiments, is a distance or amount of space sufficient to morphologically change and/or increase in size in preparation for cell division. In some embodiments, a size less than a minimum proliferation space is one that physically confines a cell to its native size, wherein the native size is the size of the whole cell and/or the cell soma while in a migratory state, a non-dividing state, and/or a non differentiating state. A cell can have a shape and size unique to its cell type and/or state of differentiation. Therefore, the native size of a cell during a migratory state, a non dividing state, and/or a non-differentiating state is further dependent on the cell type and shape. For example, the native size and shape of a hepatocyte is different than the native size and shape of a neuron, which can further be different than the native size and shape of a monocyte. The native size of a hepatocyte or monocyte, for example, is defined by the size of the whole cell during a migratory state, non-dividing state, and/or a non-differentiating state, whereas the native size of a neuron, for example, is defined, by the size of the cell soma during, a migratory state, a noon-dividing state, and/or a non-differentiating state. Additionally, a human cell can have a native size and shape different than a native size and shape of a bacterial cell, which can further have a native size and shape different than that of a fungal cell, and so on. Therefore, it should be understood by one of ordinary skill in the art that devices described herein, can comprise microchannels 101 having a cell receiving space with an average size/dimensions that is commensurate with both the cell type used and the goals of the disclosure.

In some embodiments the microchannels 101 of a device described herein can include one or more additional features. For example, in some cases, the average width 105 of the one or more microchannels 101 is less than 10 µm. The average width 105 of a microchannel 101 can be determined by measuring the width 105 of the microchannel 101 in one or more locations along the length 104 of the microchannel 101. Alternatively, an average width 105 can be determined by measuring the width 105 of two or more microchannels 101 at the same or varying locations along the length 104 of each microchannel 101. In other embodiments, the average width 105 of the one or more microchannels 101 is less than 8 µm, less than 7 µm, less than 6 µm less than 5 µm, less than 4 µm, between 2 µm and 10 µm, between 3 µm and 8 µm, or between 4 µm and 7 µm. The average width of the microchannel 101 can therefore vary. In some embodiments, the average width is selected to prevent cell proliferation within the microchannels, resulting in the exclusive presence of migrating cells within the microchannels.

The one or more microchannels 101, in some cases, are sized to receive a desired quantity of cells within the cell receiving space. For example, the cell receiving spaces of the one or more microchannels 101 can have a total internal volume equal to or greater than the volume of at least 500 migratory cells. The fraternal volume substantially corresponds to the space defined by the sidewalls 110 of the microchannels 101 and can vary in absolute value according to the cell type of the migratory cells, as cells of different origin may vary in size. In some cases, the total internal volume is equal to or greater than the volume of at least 100, at least 200, at least 300, at least 400, at least 500, at least 600, at least 700, at least 800, at least 900, or at least 1000 migratory cells.

In some embodiments, the openings 111 of the one or more microchannels 101 are fluid permeable to a liquid media via capillary action along the length 104 of the cell receiving space. For example, a liquid media comprising essential nutrients to sustain the viability of cells is readily accessible to migratory cells isolated within the microchannels 101. Whereas the openings 111 are fluid permeable, in some embodiments, the sidewalls 110 of the microchannels 101 are impermeable migratory and non-migratory cells. That is, migratory cells within the microchannels 101 can enter the openings 111 of the microchannels 101, but cannot invade into or through the walls of the microchannels 101. Migratory cells isolated within the microchannels 101 will have entered only via an opening 111 of the microchannel 101.

In other embodiments, the one or more microchannels 101 are formed from a polymer. For example, the microchannels 101, in some instances, are formed from a polysiloxane, such as polydimethylsiloxane (PDMS). Certain polymers, such as PDMS, can provide useful properties to the microchannels 101, including flexibility and durability, to prevent cracking, breaking, and/or scratching of the microchannels 101 during user manipulation of the device. The microchannels are not limited to being made only from PDMS, but can be made of any polymer that is not inconsistent with the objectives of this disclosure.

In addition, the one or more microchannels 101 of a device described herein, can be coated. A coating, in some cases, can be provided to encourage and/or promote the cell adhesion of the migratory cells to the inner surface of the microchannels 101. For example, coatings of cell adhesion-promoting substrates, including a polymeric protein, a homopolypeptide, or other cell adhesion-promoting substrates, such as poly-L-lysine or collagen, can be provided. In other cases, the one or more microchannels 101 can be coated with a pharmaceutical compound or drug to determine its effects on the migratory cell population. For example, drugs that are known or believed to inhibit cell migration or cell adhesion may be provided, such as drugs or pharmaceutical compounds being screened for their efficacy of migration-inhibiting or adhesion-inhibiting effects. In some embodiments, the one or more microchannels 101 are partially coated. Migration inhibiting and/or adhesion inhibiting compounds can be small molecules, ligands, proteins, or other biologics or biomimetics. It should be understood that any coating not inconsistent with the goals of the disclosure is contemplated.

A cell adhesion-promoting coating on the surface of microchannels 101 is different from a chemoattractant. A chemoattractant, unlike a cell adhesion-promoting coating, is intended to promote migration of the migratory cells into the microchannels 101. Furthermore, a chemoattractant, unlike a cell adhesion-promoting coating, provides a concentration gradient to guide or lead the migratory cells toward or into the microchannels 101. Therefore, in some embodiments, the microchannels 101 do not contain a chemoattractant.

In another embodiment, a device described herein is configured to be positionable in a cell culture. A cell culture, as understood by one of ordinary skill in the art, can include any one of a variety of equipment types or tools for growing and/or maintaining living cells in an artificial environment, i.e., in vitro. A cell culture can include known equipment and tools, such as a cell culture flask, a tissue culture dish or flask, a petri dish, a single well of any cell culture dish or plate, a single well of a tissue culture dish or plate, one or more interconnected wells or compartments of any cell or tissue culture dish or plate, or any other suitable in vitro environment for facilitating the attachment and/or propagation of living cells. Cell culture can further include culture media suitable for the type of cell being cultured. Cell culture media can be enhanced with various additives, including growth factors, antibiotics, or other nutrients. It is further understood, according to one of ordinary skill in the art, that a cell culture can further be placed within a larger device, compartment, or contraption conducive to facilitating and/or sustaining the life of the cells in vitro, e.g., an incubator or other controlled environment. These and other embodiments of a cell culture, as understood by one of ordinary skill in the art, are contemplated.

II. Methods of Isolating a Migratory Cell Population

Figure 8:
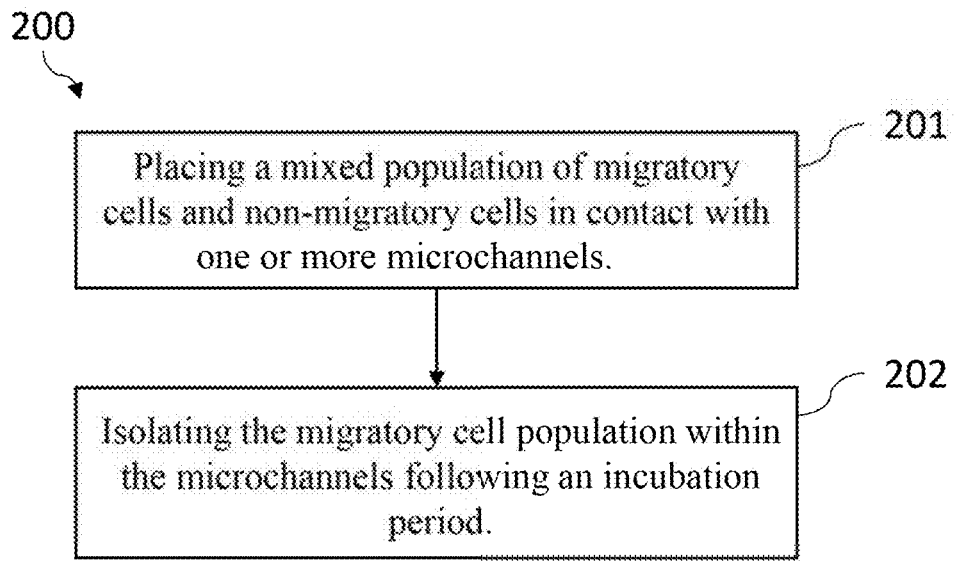
FIG. 8 is a block diagram of a method of isolating a migratory cell population.

In another aspect, methods of isolating a migratory cell population from a mixed population of migratory cells and non-migratory cells are described herein. As shown in FIG. 8, a method 200 comprises placing the mixed population of migratory cells and non-migratory cells in contact with one or more microchannels at step 201, and isolating the migratory cell population within the microchannels following an incubation period at step 202. In some embodiments, a method 200 described herein further comprises collecting the migratory cell population from the microchannels following an incubation period. Features and characteristics of the one or more microchannels 100 used in methods described herein can include features and characteristics of the one or more microchannels 101 described for the devices in Section I herein. For example, the one or more microchannels 101 have a minimum proliferation direction, a minimum proliferation space, a length 104, a width 105, and a height 103 that are substantially the same as described in Section I. Other features and characteristics of the one or more microchannels 101 of methods described herein are also described in Section I.

Now turning to specific steps of the method, placing the mixed population of migratory cells and non-migratory cells in contact with one or more microchannels 101 means the population of migratory cells and non-migratory cells and the microchannels 101 are placed at least within a reasonable distance from each other to allow the migratory cells to migrate into the microchannels 101. The mixed population of migratory cells and non-migratory cells, in some cases, can be physically touching the microchannels 101 when placed in contact. In other cases, the mixed population of migratory and non-migratory cells are separated. A reasonable separation between the mixed population and microchannels 101, as understood by one of ordinary skill in the art, can be any distance across a surface and/or a medium that a single cell can migrate into the microchannels 101 via propulsion of a cellular migration process, e.g. flagella, cilia, pseudopodia, lamellipodia, or other cytoskeleton-based method of cellular movement. In some instances, the mixed population of migratory cells and non-migratory cells are placed proximate, adjacent, or in the vicinity of openings 111 to the microchannels 101, thereby facilitating opportunity for the migratory cells to enter the microchannels 101 via the openings 111. For example, placing the mixed population of migratory cells and non-migratory cells in contact with one or more microchannels 101 includes placing the mixed population of migratory cells and non-migratory cells in the same compartment and/or in the same environment, such as in a cell culture.

In some embodiments, the one or more microchannels 101 are disposed or positioned in a cell culture. A cell culture, as understood by one of ordinary skill in the art, can include any one of a variety of techniques, tools, and/or equipment for growing and/or maintaining living cells in an artificial environment, i.e. in vitro. The types of cells used for a cell culture include any living cell type from one of the six kingdoms of life: Archaebacteria, Eubacteria, Protists, Fungi, Plants, and/or Animals. A cell culture includes known equipment and tools, such as a cell culture flask, a tissue culture dish or flask, a petri dish, a single well of any cell culture dish or plate, a single well of a tissue culture dish or plate, one or more interconnected wells or compartments of any cell or tissue culture dish or plate, or any other suitable in vitro environment for facilitating the attachment and/or propagation of living cells. A cell culture can further include culture media suitable for the type of cell being cultured. Cell culture media can be enhanced with various additives, including growth factors, antibiotics other nutrients. It is further understood, according to one of ordinary skill in the art, that a cell culture can further be placed within a larger device, compartment, or contraption conducive to facilitating and/or sustaining the life of the cells in vitro, e.g. an incubator or other controlled environment. These and other embodiments of a cell culture, as understood by one of ordinary skill in the art, are contemplated.

In some embodiments, the mixed population of migratory cells and non-migratory cells is placed in contact with a plurality of microchannels 101, and, the microchannels 101 comprise an array. A plurality of microchannels 101 can include two or more microchannels 101. Features and characteristics of microchannels 101 disposed in an array of methods described herein are also described in the devices of Section I.

In some embodiments of method 200, placing the mixed population migratory cells and non-migratory cells in contact with one or more microchannels 101 comprises seeding the mixed population proximate an opening to the one or more microchannels 101. For example, in some cases, one or more microchannels 101 are placed in a cell culture prior to introducing the mixed population of cells. Cells are then seeded adjacent to or proximate an opening 111 to the one or more microchannels 101. Seeding cells adjacent to or proximate an opening to the one or more microchannels 101 should be performed with caution so as to prevent any cells from floating into the microchannels 101 and/or occluding, or otherwise blockading, an opening to the one or more microchannels 101.

In other embodiments, placing the mixed population of migratory cells and non-migratory cells in contact with one or more microchannels 101 comprises placing the one or more microchannels adjacent to seeded cells of the mixed population. For example, in some cases, a mixed population of migratory and non-migratory cells are first seeded in a cell culture prior to introducing the one or more microchannels 101 into the cell culture. The one or more microchannels 101 are then placed adjacent to or among the seeded cells. Prior to placing the one or more microchannels 101 adjacent to or among the seeded cells, a scratch or clearing can be introduced to the seeded cells so as to mark a location for placing the one or more microchannels 101 in contact with the mixed population, of migratory cells and non-migratory cells In some embodiments, placing the mixed population of migratory cells and non-migratory cells in contact with one or more microchannels 101 comprises removing a barrier between the mixed population of migratory cells and non-migratory cells and the one or more microchannels 101. The mixed population of migratory and non-migrators cells, in some embodiments, are seeded in a compartment having a removable barrier. The compartment can be a cell culture dish, a petri dish, a well of a cell culture dish, or any other space or environment suitable for a cell culture. The microchannels 101 are placed on the opposite side of the removable barrier, either before or after the cells are seeded. The removable barrier, in some embodiments, provides a temporary cell-free space to place the microchannels 101 in the compartment. In other embodiments, the removable barrier prevents unintentional and/or inadvertent floating of the mixed population of cells into the one or more microchannels 101 during seeding of the mixed population. For example, the removable barrier can block opening 111 of the microchannels 101 The barrier can be removed prior to commencing an incubation period. For example, the barrier can be removed once the mixed population of cells has settled and/or attached to a surface of the cell culture.

In another aspect, method 200 described herein comprises isolating the migratory cell population within the microchannels 101 following an incubation period, isolating the migratory cell population, in some cases, includes selectively isolating the migratory cells from the mixed population. For example, during an incubation period only the migratory cells migrate into the microchannels 101. In some embodiments, a method 200 includes incubating the mixed population of migratory cells and non-migratory cells and allowing the migratory cells to migrate into the microchannels 101 during an incubation period. Migratory cells isolated within the microchannels 101, in some embodiments, are cells that are actively migrating. In other embodiments, migratory cells isolated within the microchannels 101 are cells that have migrated and subsequently entered a state of quiescence or senescence. Migratory cells isolated within the microchannels 101 are not proliferating and/or dividing cells.

An incubation period, as understood by one of ordinary skill in the art, is any length of time sufficient to allow the migratory cells to migrate into the microchannels 101. For example, in some embodiments, an incubation period can be between 1 day and 21 days, between 2 days and 14 days, between 3 days and 10 days, between 4 days and 8 days, or between 5 days and 7 days. In other embodiments, an incubation period can be at least 1 hr, at least 3 hrs, at least 6 hrs, at least 12 hrs, at least 24 hrs, at least 2 days, at least 3 days, at least 5 days, at least 7 days, at least 10 days, at least 14 days, or at least 21 days. Alternatively, an incubation period can be less than 21 days, less than 14 days, less than 10 days, less than 7 days, less than 5 days, less than 3 days, less than 2 days, less than 24 hrs, less than 12 hrs, less than 6 hrs, less than 3 hrs, or less than 1 hr.

The length of an incubation period, in some embodiments, is defined by a desired quantity of cells that have migrated into the microchannels 101. That is, an incubation period, in some cases, ends after at least a desired quantity of cells have migrated into the one or more microchannels 101. In some instances, the length of an incubation period is dependent on the type of cells, as some cell types migrate faster or slower than other cell types. For example, metastatic cancer cells or activated immune cells can migrate at a different speed than normal and/or inactivated cells. In some embodiments, a desired quantity of cells is at least 100, at least 200, at least 300, at least 400, at least 500, at least 600, at least 700, at least 800, at least 900, or at least 1000 cells. For example, in some embodiments of a method described herein, at least 500 migratory cells are isolated within the microchannels 101. In other embodiments, at least 600, at least 700, at least 800, at least 900, or at least 1000 migratory cells are isolated within the microchannels. It should be readily understood that any incubation period not inconsistent with the goal of this disclosure is also contemplated.

In some embodiments, isolating the migratory cell population within the microchannels 101 following an incubation period comprises removing the non-migratory cells from contact with the microchannels. For example, the non-migratory cells can be scraped off and/or aspirated away from the microchannels 101. Importantly, removing the non-migratory cells from contact with the microchannels 101 should be performed with caution so as to not disturb and/or cause detachment of the migratory cells within the microchannels 101.

In another embodiment, isolating the migratory cell population within the microchannels 101 following an incubation period comprises removing the microchannels 101 from a cell culture. Microchannels 101 removed from a cell culture are physically separated from the mixed population of migratory and non-migratory cells following an incubation period. In some cases, the microchannels 101 are removed by peeling. For example, the microchannels 101 can be peeled from the surface a cell culture dish or a glass surface positioned within a cell culture. In other embodiments, the one or more microchannels 101 are on an extractable surface, such as a glass cover slip, and the extractable surface with the microchannels 101 is removed from the cell culture.

In some instances, a method 200 of isolating a migratory cell population from a mixed population of migratory cells and non-migratory cells further comprises collecting the migratory cell population from the microchannels 101 following an incubation period. Collecting the migratory cell population from the microchannels 101, in some embodiments, occurs in a cell culture. In these embodiments, the non-migratory cells can be first removed from the cell culture prior to collecting the migratory cell population. Still, collecting the migratory cell population from the microchannels 101 can occur upon removing the microchannels 101 from a cell culture. Furthermore, collecting the migratory cell population from the microchannels 101, in some embodiments, comprises extracting the migratory cell population from inside the microchannels 101. For example, the migratory cell population, in some instances, is scraped off and/or eluted from the microchannels 101. Elution of the migratory cell population is performed with a liquid solution, wherein exposure of the migratory cells in the microchannels 101 to the liquid solution results in their detachment and/or release from the microchannels 101. It should be readily understood that an liquid solution or extraction method not inconsistent with the goal of the disclosure is also contemplated.

In other embodiments, collecting the migrators cell population from the microchannels 101 comprises extracting the molecular contents of the migratory cell population from inside the microchannels 101, for example, by exposing the migratory cell population within the microchannels 101 to a detergent or lysis buffer. A lysis buffer, as understood by one of ordinary skill in the art, can include detergents, salts, and/or enzymes suitable to preserve structural integrity of molecular components of a migratory cell and/or allow access to molecular targets of the migratory cell, either by permeablizing and/or lysing the cell. For example, exposing the migratory cell population to a detergent can, in some cases, include exposing the DNA, RNA, sugars, proteins, and/or lipids of the migratory cell population within the microchannels 101. In some instances, the migratory cell population can be first fixed by a fixing agent, such as formaldehyde, paraformaldehyde, formalin, or methanol. In other cases, a permeabilizing buffer and fixing agent can be used simultaneously.

In other embodiments, collecting the migratory cell population from the microchannels 101 comprises exposing the migratory cell population to a protease enzyme. A protease enzyme suitable to migratory cell population can be any enzyme or combination of enzymes causing disruption of cell adhesion and/or detachment of the migratory cells from the microchannels 101. Therefore, exposure of the migratory cell population to a protease enzyme allows extraction of the migratory cell population in their viable, whole-cell form. In some embodiments, the microchannels 101 can be coated with one or more cell adhesion-promoting substrates, including a polymeric protein, a homopolypeptide, or other cell adhesion-promoting substrate, such as poly-L-lysine. Therefore, in some cases, a protease enzyme disrupts adhesion of the migratory cell population to a coating of the microchannels 101 and/or causes detachment of the migratory cell population from a coating of the microchannels 101. Trypsin is an exemplary enzyme that disrupts cell adhesion and is commonly used in practice to detach cells in vitro from a surface. Other trypsin-like enzymes, combination of enzymes, or solutions can be used to achieve the desired result. It should be readily understood by one of ordinary skill in the art that any protein, peptide, or amino acid not inconsistent with the goal of the disclosure is also contemplated.

III. Methods of Analyzing a Migratory Cell Population

Figure 9:
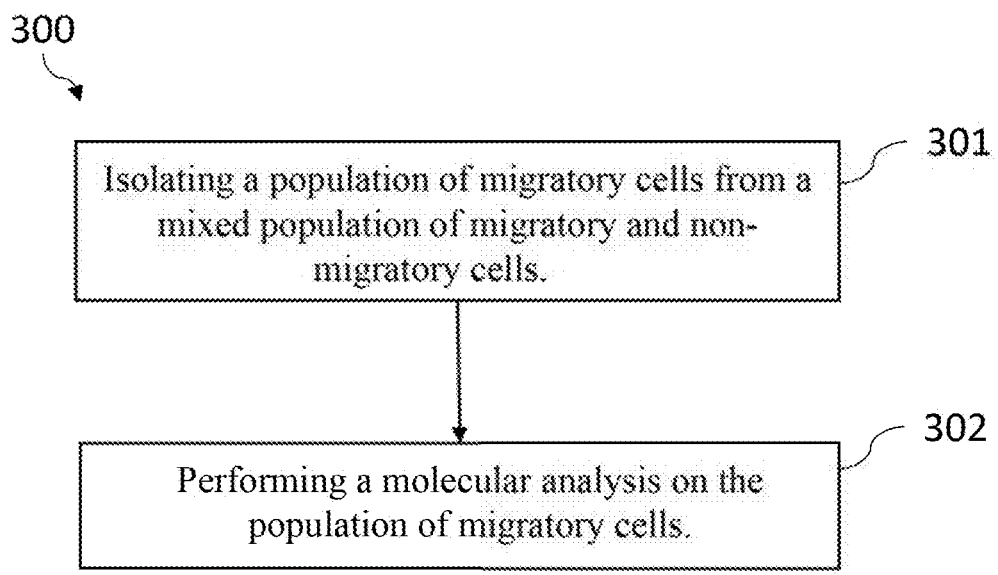
FIG. 9 is a block diagram of a method of analyzing a migratory cell population.

In another aspect, methods of performing molecular analysis are provided herein. As shown in FIG. 9, a method 300 comprises isolating a population of migratory cells from a mixed population of migratory and non-migratory cells at step 301, and performing a molecular analysis on the population of migratory cells at step 302, wherein the population of migratory cells includes at least 500 cells. The population of migratory cells isolated according to method 300 can be a pure or substantially pure population of migratory cells. A "pure" population of migratory cells, for reference purposes herein, is a population of cells that includes only migratory cells, as opposed to non-migratory cells. However, it is to be understood that a pure population of migratory cells can include migratory cells of various types. It is further to be understood that a method described herein may result in the isolation of a population of cells that is not completely "pure", e.g. due to contamination or other experimental error or anomaly. A "substantially" pure population of migratory cells, for reference purposes here, includes a population of cells that includes at least 80%, at least 85%, at least 90%, at least 95%, or at least 99% migratory cells, based on the total number of cells isolated, wherein the balance of cells can include non-migratory cells.

In some embodiments, method 300 comprises isolating a population of migratory cells from a mixed population of migratory and non-migratory cells. Isolating a migratory cell population, as described in methods of performing molecular analysis, can include any one or more of the steps and/or features of the method 200 of isolating a migratory cell population described in Section II herein, including, but not limited to, placing the mixed population of migratory cells and non-migratory cells in contact with one or more microchannels 101 and collecting the migratory cell population from the microchannels 101 following an incubation period. Additional steps of features of a method of performing molecular analysis described herein, can also be described in detail of Section II herein.

Furthermore, method 200 of isolating a migratory cell population of Section II references features and characteristics of the one or more microchannels 101 of devices for isolating a migratory cell population in Section I, methods of performing molecular analysis can also contain any one or more of the features and characteristics of the one or more microchannels 101 described in Section I herein, including, but not limited to the one or more microchannels 101 having an average size in a proliferation direction of the migratory cells that is less than a minimum proliferation space of the migratory cells along the proliferation direction. These and other features and characteristics of the one or more microchannels 101 used in a method of performing molecular analysis are described in detail of Section I herein.

In other embodiments, method 300 can include any one or more of a proteomic, metabolomic, glycomic, lipidomic, transcriptomic, epigenomic, genomic and/or other "-omic" analysis known to the skilled artisan. Various methods and techniques for performing these types of analyses can be used to detect target molecules, including, but not limited to: proteins and protein modifications such as phosphorylation, ubiquitination, methylation, acetylation, glycosylation, oxidation and/or nitrosylation; RNAs, such as tRNA, mRNA, rRNA, siRNA, miRNA, piRNA, lncRNA, and/or snoRNA; any of the molecules known to contribute to a metabolome, including endogenous and exogenous metabolites; epigenetic modifications, such as acetylation, methylation, ubiquitylation, phosphorylation, sumoylation, ribosylation and citrullination and/or other covalent modifications; and/or genetic sequences found in either genomic DNA and/or mitochondrial DNA.

Furthermore, method 300 as described herein, can include any one or more methods or techniques for detecting a molecular target, including, but not limited to: Western Blot, immunohistochemistry, enzyme-linked immunosorbent assay (ELISA), mass spectrometry, spectroscopy, nanopore sensing, SDS-PAGE, microarray, chromatography, multiple reaction monitoring, mass spectrometry, NMR spectroscopy, Northern Blot, RNA-Seq, RT-PCR, qRT-PCR, chromatin immunoprecipitation, ChIP-on-chip, ChIP-Seq, fluorescent in situ hybridization, methylation-sensitive restriction enzymes, DNA adenine methyltransferase identification (DamID), bisulfite sequencing, Southern Blot, PCR, Geisma banding or other karyotyping, and/or any one or more types of DNA sequencing technologies. As understood by one of ordinary skill in the art, other known techniques and technologies suitable for detecting proteins, protein modifications, sugars, lipids, and/or nucleic acids of the migratory cell population can be used in the methods disclosed herein. It should be understood that a method of performing molecular analysis as described herein can include these and any other molecular analyses not inconsistent with the goal of the disclosure.

Many modifications and other embodiments of the subject matter will come to mind to one skilled in the art to which the subject matter pertains having the benefits of the teachings presented in the foregoing descriptions and the associated drawings. For example, although specific configurations of microchannels 101 are described above and depicted in the figures, numerous other microchannel arrays or stand-alone microchannels 101 configured to isolate a migratory cell population may benefit from embodiments of the subject matter described herein. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

Various implementations of devices and methods have been described, and exemplary embodiments are described below in fulfillment of various objectives of this disclosure. It should be recognized that these implementations are merely illustrative of the principles of this disclosure. Numerous modifications and adaptations thereof will be readily apparent to those skilled in the art without departing from the spirit and scope of this disclosure. For example, individual steps of methods described herein can be carried out in any manner not inconsistent with the objectives of this disclosure, and various configurations or adaptations of devices described herein may be used.

IV. Selected Embodiments

Although the above description and the attached claims disclose a number of embodiment of the invention, other alternative aspects of the invention are disclosed in the following further embodiments.

Embodiment 1. A method of isolating a migratory cell population from a mixed population of migratory cells and non-migratory cells, the method comprising:
placing the mixed population of migratory cells and non-migratory cells in contact with one or more microchannels; and
isolating the migratory cell population within the microchannels following an incubation period,
wherein the one or more microchannels have an average size in a proliferation direction of the migratory cells that is less than a minimum proliferation space of the migratory cells along the proliferation direction.

Embodiment 2. The method of embodiment 1 further comprising collecting the migratory cell population from the microchannels.

Embodiment 3. The method of embodiment 1 or 2, wherein the proliferation direction is horizontal and the mixed population of cells are eukaryotic.

Embodiment 4. The method of embodiment 1 or 2, wherein the proliferation direction is vertical and the mixed population of cells are microbial.

Embodiment 5. The method of any preceding embodiment, wherein the microchannels do not contain a chemoattractant.

Embodiment 6. The method of any preceding embodiment, wherein the mixed population is placed in contact with a plurality of microchannels, and the plurality of microchannels comprise an array.

Embodiment 7. The method of any preceding embodiment, wherein the microchannels are positioned in a cell culture.

Embodiment 8. The method of any preceding embodiment, wherein the one or more microchannels has an average width of less than 10 μm.

Embodiment 9. The method of any preceding embodiment, wherein the microchannels are open on a side.

Embodiment 10. The method of any of embodiments 1-8, wherein the microchannels are enclosed by an upper wall.

Embodiment 11. The method of any preceding embodiment, wherein at least 500 migratory cells are isolatable within the microchannels.

Embodiment 12. The method of any preceding embodiment, wherein each of the microchannels comprise an opening permeable to a liquid media via capillary action along the length of the microchannels.

Embodiment 13. The method of any preceding embodiment, wherein the microchannels have sidewalls that are impermeable to the migratory and non-migratory cells.

Embodiment 14. The method of any preceding embodiment, wherein the one or more microchannels are formed from a polymer.

Embodiment 15. The method of any preceding embodiment, wherein the microchannels are formed from a polysiloxane.

Embodiment 16. The method of embodiment 1, wherein placing the mixed population of migratory cells and non-migratory cells in contact with one or more microchannels comprises seeding the mixed population proximate an opening on an end of each of the microchannels.

Embodiment 17. The method of embodiment 1, wherein placing the mixed population of migratory cells and non-migratory cells in contact with one or more microchannels comprises placing the one or more microchannels adjacent to seeded cells of the mixed population.

Embodiment 18. The method of embodiment 1, wherein isolating the migratory cells within the microchannels comprises removing the non-migratory cells from contact with the microchannels.

Embodiment 19. The method of embodiment 7, wherein isolating the migratory cells within the microchannels comprises removing the microchannels from the cell culture.

Embodiment 20. The method of embodiment 2, wherein collecting the migratory cell population from the microchannels comprises extracting the migratory cell population from inside the microchannel.

Embodiment 21. The method of embodiment 2, wherein collecting the migratory cell population from the microchannels comprises exposing the migratory cell population to a protease enzyme.

Embodiment 22. A device for isolating migratory cells from a mixed population of migratory cells and non-migratory cells, the device comprising:
one or more microchannels having an average size in a proliferation direction of the migratory cells that is less than a minimum proliferation space of the migratory cells along the proliferation direction.

Embodiment 23. The device of embodiment 22, wherein two or more of the microchannels comprise an array.

Embodiment 24. The device of embodiment 22 or 23, wherein the microchannels are open on a side.

Embodiment 25. The device of embodiment 22 or 23, wherein the microchannels form a conduit enclosed by four connected sidewalls.

Embodiment 26. The device of any one of embodiments 22-25, wherein the one or more microchannels has an average width of less than 10 μm.

Embodiment 27. The device of any one of embodiments 22-26, wherein the one or more microchannels have a total internal volume equal to or greater than the volume of at least 500 migratory cells.

Embodiment 28. The device of any one of embodiments 22-27, wherein the one or more microchannels are permeable to a liquid media.

Embodiment 29. The device of any one of embodiments 22-28, wherein the one or more microchannels are formed from a polymer.

Embodiment 30. The device of embodiment 29, wherein the polymer is impenetrable to the migratory cells.

Embodiment 31. The device of any one of embodiments 22-30, wherein the microchannels are coated.

Embodiment 32. The device of any one of embodiments 22-31, wherein the device further comprises a cell culture and the microchannels are disposed in the cell culture.

Embodiment 33. A method of performing molecular analysis, the method comprising:
isolating a population of migratory cells from a mixed population of migratory and non-migratory cells; and
performing a molecular analysis on the population of migratory cells,
wherein the population of migratory cells includes at least 500 cells.

Embodiment 34. The method of embodiment 33, wherein isolating a population of migratory cells comprises:
placing the mixed population of migratory cells and non-migratory cells in contact with one or more microchannels; and
collecting the migratory cell population from the microchannels following an incubation period,
wherein the one or more microchannels have an average size in a proliferation direction of the migratory cells that is less than a minimum proliferation space of the migratory cells along the proliferation direction.

Embodiment 35. The method of embodiment 34, wherein the proliferation direction is horizontal and the mixed population of cells are eukaryotic.

Embodiment 36. The method of embodiment 34, wherein the proliferation direction is vertical and the mixed population of cells are microbial.

Embodiment 37. The method of any one of embodiments 34-36, wherein the microchannels are free from a chemoattractant.

Embodiment 38. The method of any one of embodiments 33-37, wherein the mixed population is placed in contact with a plurality of microchannels, and the microchannels comprise an array.

Embodiment 39. The method of any one of embodiments 34-38, wherein the microchannels are positioned in a cell culture.

Embodiment 40. The method of any one of embodiments 34-39, wherein the one or more microchannels has an average width of less than 10 µm.

Embodiment 41. The method of any one of embodiments 34-40, wherein the microchannels are open on a side.

Embodiment 42. The method of any one of embodiments 34-40, wherein the microchannels comprise a longitudinally extending cell receiving space formed by four connected sidewalls.

Embodiment 43. The method of any one of embodiments 34-42, wherein openings of the microchannels are permeable to a liquid media via capillary action along the length of the microchannels.

Embodiment 44. The method of any one of embodiments 34-43, wherein sidewalls of the microchannels are impermeable to the migratory and non-migratory cells.

Embodiment 45. The method of any one of embodiments 34-44, wherein the one or more microchannels are formed from a polymer.

Embodiment 46. The method of any one of embodiments 34-45, wherein the microchannels are formed from a polysiloxane.

Embodiment 47. The method of any one of embodiments 34-46, wherein placing the mixed population of migratory cells and non-migratory cells in contact with one or more microchannels comprises seeding the mixed population proximate an opening on an end of the one or more microchannels.

Embodiment 48. The method of any one of embodiments 34-46, wherein placing the mixed population of migratory cells and non-migratory cells in contact with one or more microchannels comprises placing the one or more microchannels adjacent to seeded cells of the mixed population.

Embodiment 49. The method of any one of embodiments 33-48, wherein isolating the migratory cells within the microchannels comprises removing the non-migratory cells from contact with the microchannels.

Embodiment 50. The method of embodiment 33, wherein isolating the migratory cells within the microchannels comprises removing the microchannels from the cell culture.

Embodiment 51. The method of any one of embodiments 34-50, wherein collecting the migratory cell population from the microchannels comprises extracting the migratory cell population from inside the microchannels.

Embodiment 52. The method of any one of embodiments 34-51, wherein collecting the migratory cell population from the microchannels comprises exposing the migratory cell population to a protease enzyme.

Embodiment 53. The method of any one of embodiments 33-52, wherein the molecular analysis is a proteomic analysis.

Embodiment 54. The method of any one of embodiments 33-52, wherein the molecular analysis is a metabolomic analysis.

Embodiment 55. The method of any one of embodiments 33-52, wherein the molecular analysis is a transcriptomic analysis.

Embodiment 56. The method of any one of embodiments 33-52, wherein the molecular analysis is a genomic analysis.

Some embodiments described herein are further illustrated in the following non-limiting examples.

Example 1

Design and Fabrication of a Device for Isolating a Migratory Cell Population

Figure 2:
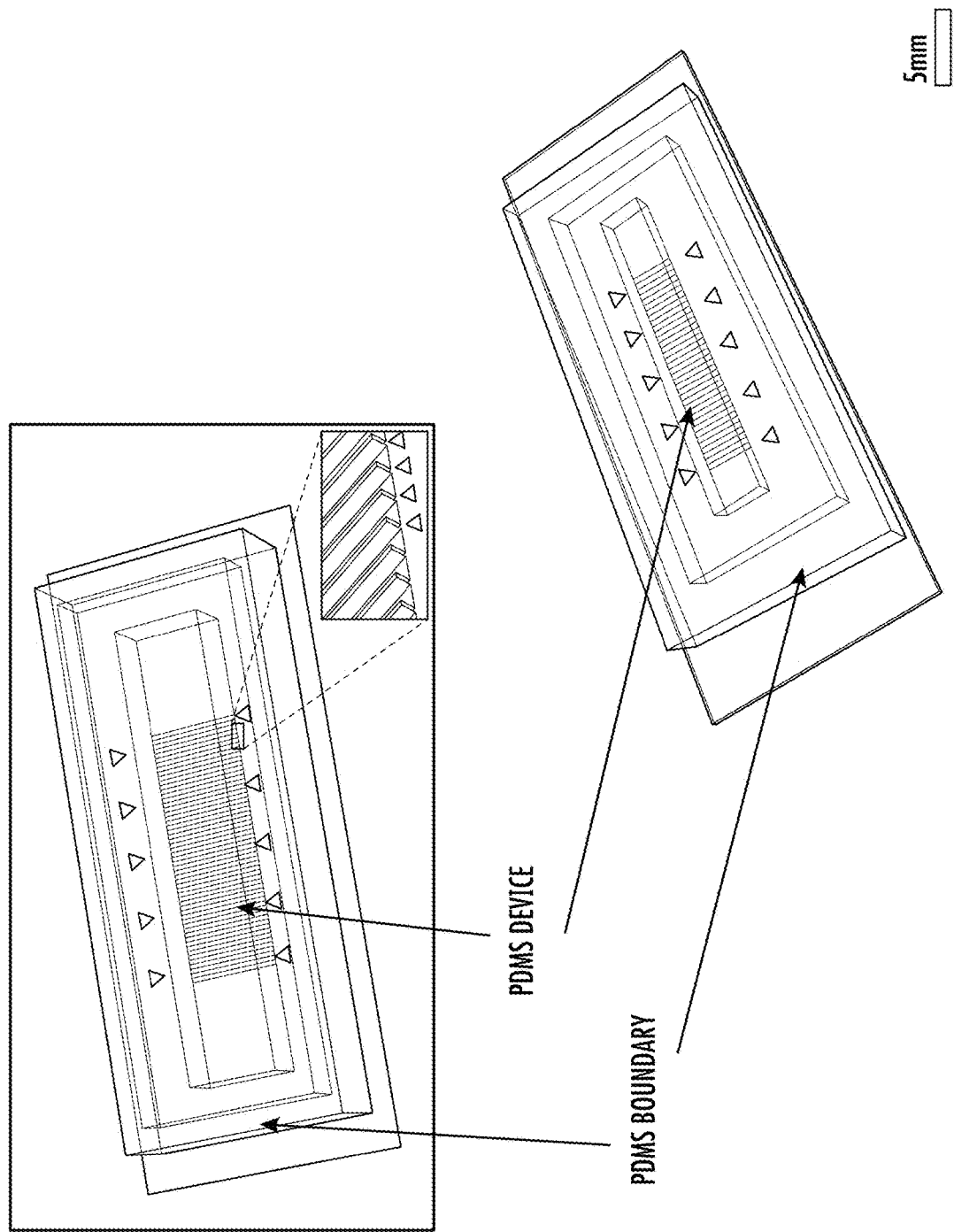
FIG. 2 is a schematic view of a microchannel containing device and a photograph of a microchannel containing device.

A microchannel array comprising a total of 600 parallel microchannels 101 was prepared, each microchannel 101 having a configuration shown in FIG. 1A. Each microchannel 101 had a cross sectional area of 5 µm×12 µm (width× height) generating a sufficient 3D physical confinement for cell migration. To facilitate recruitment of a large quantity of migrating cells, the microchannels 101 were 5 mm in length. A distance of 30 µm between every two microchannels 101 allowed visualization of cells within the microchannels 101. The whole array of microchannels 101 was approximately 5 mm×21 mm (total length×total width). In addition to the microchannels 101, a boundary was designed to create a closed well for holding medium during cell culture. A 3D representation of a microchannel-containing device placed on top of a cover glass slip and inside a PDMS boundary is shown in FIG. 2.

Fabrication of the microchannel array was conducted using standard photolithography and soft lithography. Briefly, the microchannel feature was photo-patterned on a silicon wafer coated with SU-8 photoresist. The thickness of the photoresist was 12 µm, which also defined the microchannel height. A mixture of Polydimethylsiloxane (PDMS and a curing agent (10:1 v/v) was cast onto the wafer and baked for 10 minutes at 150° C. The cured PDMS was carefully peeled from the wafer, and cut to create entrance inlets (i.e., openings 111) for all microchannels 101. Thus the final microchannel length 104 was shorter than 5 mm, and depending on the manual cutting process, where the length 104 varied front approximately 3 mm to 4 mm.

Example 2

Isolation and Quantification of a Migratory Cell Population from a Mixed Population of Migratory and Non-Migratory Cells Microchannel devices as described in Example 1 were prepared. Each device was decontaminate with 70% ethanol and assembled onto sterile cover glass as shown in FIG. 2. Cells from the human glioblastoma cell line G55 were cultured in serum-free DMEM/F-12 media supplemented with 1×B-27, 1× Insulin-Transferrin-Selenium-X, and mouse EGF. A suspension of mixed migratory and 2D/non-migratory cells ($50×10^3$ cells/array) Were introduced at the microchannel entrances to facilitate the initiation of migration via confinements, and maintained up to 7 days to obtain the highest number of migrating cells. As a control, the PDMS microchannel array was replaced with a plain PDMS block and cells were grown on the cover glass surface.

The culture medium was aspirated from the experimental device. Cells were then washed twice with PBS. All unnecessary non-migrating cells from the mixed population were removed using Costar® 3008 Cell Lifter (Corning Inc.) and verified under the microscope.

To visualize the migrating cells inside the microchannels, Hoechst® 33342 (Invitrogen) fluorescent dye was used to stain their nuclei. Cells were introduced to the dye solution (5 μg/ml) and incubated overnight. On the next day, videos of fluorescent signals of the entire intact microchannel device were recorded.

Using tweezers the PDMS microchannel array was then disassembled or peeled off from the cover glass to expose the migrating cells. Notably, migrating cells were found to be on both disassembled PDMS microchannels and the cover glass. For control devices, similar steps of washing with PBS, removal of PDMS boundary and PDMS block were conducted. Then cells on the cover glass surface were collected.

Quantifications by counting both the initial migrating cells via microchannels 101 and the post-peeling migrating cells were performed (n=5 devices). Results shown in FIG. 3 show cells migrating and isolated within the microchannels and a quantification of the migratory cell population of intact microchannels and microchannels after peeling. According to the quantification results of Hoechst® stained for nuclei, there were 2,730 (±1,019) migrating cells present within the intact microchannels (i.e., before peeling off). After peeling, the number of cells in the PDMS microchannels and on the cover glass was 934 (±193) and 1,182 (±380), respectively. After peeling, migratory cells were scraped from both inside the microchannels and on the cover glass, and the efficacy of cell collection was determined to be approximately 77%.

Example 3

Whole-Cell Collection of a Migratory Cell Population

Figure 5:
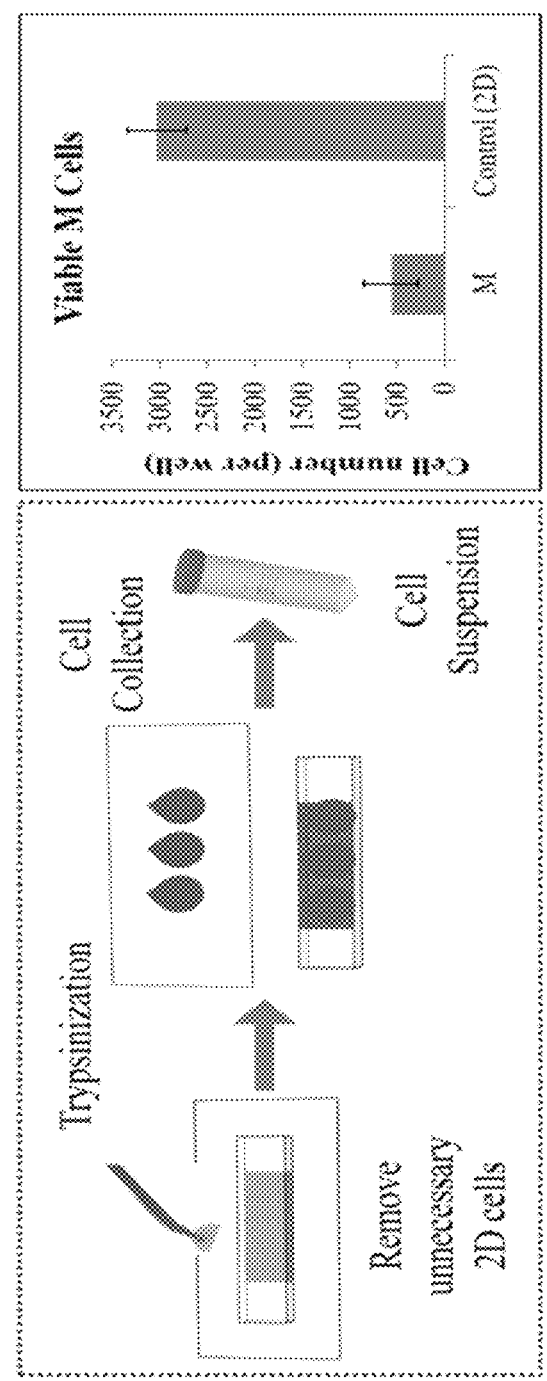
FIG. 5 shows a process of collecting whole migratory cells isolated within microchannels and a graphical view of the migratory cell viability.

Microchannel devices as described in Example 1 were prepared. Each device was decontaminate with 70% ethanol and assembled onto sterile cover glasses as shown in FIG. 2. Cells from the human glioblastoma cell G55 were cultured in serum-free DMEM/F-12 media supplemented with 1×B-27, 1× Insulin-Transferrin-Selenium-X, and mouse EGF. A suspension of mixed migratory and non-migratory cells ($50 \times 10^3$ cells/array) were introduced at the microchannel entrances (i.e., openings 111) to facilitate the initiation of migration via confinements, and maintained up to 7 days to obtain the highest number of migrating cells. The culture medium was aspirated from the device. Cells were washed twice with PBS. Using tweezers the PDMS boundary was removed from the cover glass surface. For exclusive extraction of the migrating cells and their contents, decontamination of non-migratory cells was performed. Non-migratory cells were stripped using Costar® 3008 Cell Lifter (Corning Inc.) and verified under the microscope. The PDMS microchannel device was disassembled from the glass surface to expose the migrating cells for whole cell collection. Migratory cells were collected from both the disassembled PDMS microchannels 101 and the cover glass using trypsinization as shown in the method of FIG. 5. Cells collected from five peeled devices were evaluated for viability by MTS Assay. For the control, 2D/mixed population of non-migratory and migratory cells were seeded at 2,500 cells per well. After 24 hour recovery, the number of viable migrating and 2D/mixed population of cells was 568 (±283) and 3,029 (±312), respectively (FIG. 5). Therefore, approximately 114 viable migrating cells were obtained from each device.

Example 4

Protein Collection from Isolated Migratory Cells and Western Blot Analysis

Migratory cells were isolated according to Example 2. A mixture of RIPA Lysis buffer (Sigma-Aldrich) and protease inhibitor cocktail (P2714, Sigma-Aldrich) was introduced directly to the cell containing areas (FIG. 4) and allowed 30 min at 4° C. for complete protein extraction (n=8 devices for migrating cells, n=1 device for 2D/mixed population cells). Then, centrifugation was employed to eliminate insoluble cellular debris. The supernatant protein lysate was stored at −20° C. for subsequent use. The protein lysate could be concentrated by Amicon® Ultra centrifugal filter (Milipore). Total protein concentration was estimated using the Coomassie Plus™ Protein Assay (Thermo Scientific).

The proteins were first separated by their molecular weights using standard 10% SDS-PAGE (estimated 15-20 μg protein/well). After electrophoresis, the gel was stained with Brilliant Blue G 250 (Sigma-Aldrich) to visualize the available total protein for immunoblotting. The image of the gel was taken, and the total protein of migrating cells and 2D/mixed population cells was verified on the basis of densitometric analysis using linage J and Excel.

For blotting, the gel was electrotransferred onto a PVDF membrane (Bio-Rad) with transfer buffer (25 mM Tris, 192 mM glycine, 20% methanol). The membranes were blocked in 5% dry milk blocking solution at 4° C. for 90 minutes. Primary antibodies were also prepared in the blocking solution. Incubation of primary antibodies to the membrane was conducted at 4° C. overnight. The next day, the membrane was washed with TBST (Tris-buffered Saline, 0.1% Tween 20). Secondary peroxidase antibodies were prepared in the TBST. The membrane was incubated with the secondary antibody at room temperature for 2 hours and then washed with TBST. The chemiluminescent substrate (Santa Cruz Biotechnology) was introduced to the membrane and signals of the target protein on X-ray Film (Lightlabs) were developed using a film processor (Mini-Med, AFP Imaging).

Mouse anti-Vimentin (1:1000, Invitrogen), mouse anti-Met (1:1000, Cell Signaling Technology) and mouse anti-β3-Tubulin (1:1000, Cell Signaling Technology) were used as primary antibodies to detect protein expression. Anti-mouse IgG (Sigma-Aldrich) was used as a secondary peroxidase antibody. All protein related experiments were performed in triplicate. The result on X-ray film was scanned, and signals were quantified using Image J and Excel. The normalized signal was calculated by dividing intensity of the target protein to the corresponding total protein intensity measured from the gel.

Figure 6:
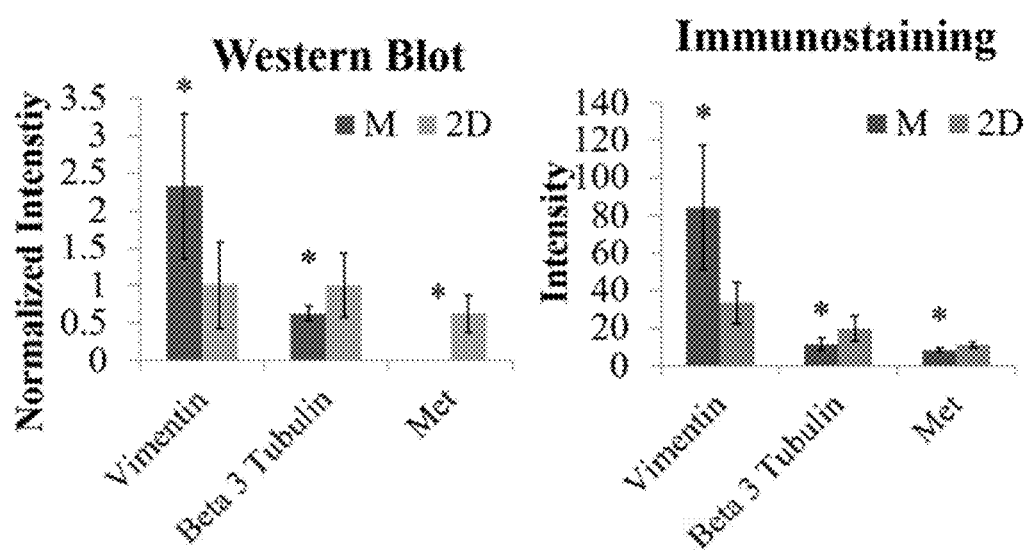
FIG. 6 is a graphical representation of quantitative results from Western Blot and Immunohistochemistry analysis of a migratory cell population isolated using the array of FIG. 1A.

Protein concentrations were estimated by Coomassie Plus™ Protein Assay for migrating and 2D/mixed population cells to be 496 (±240) and 1822 (±742) μg/ml, respectively. The samples introduced to the gel, after equalizing the concentration, contained about 15-20 μg protein per well. Densitometric analysis of the gel revealed that the protein availability of the 2D/mixed population cells was approximately 4 times higher than migrating cells. Western blot results (FIG. 6) revealed significantly increased signals of Vimentin in migrating cells compared to 2D/mixed population cells, and significantly increased of β3-Tubulin and Met in the 2D/mixed population cells compared to migrating cells. Notably, Met levels in migrating cells was undetectable via Western Blot analysis.

This example demonstrates compatibility of instant disclosure to the Western Blot protocol. For example, during SDS-PAGE, 10-50 μg of protein is typically required for a mini-well loading 19, and depending on the cell size, 12,500-25,000 cells are enough for such amount 20. More than 2,000 migrating cells were accessed per device (FIG. 3), thus eight microchannel devices provided a sufficient amount of protein for gel electrophoresis.

Example 5

Isolation and Immunohistochemistry Analysis of a Migratory Cell Population

Migratory cells were isolated from the mixed population as in Example 2. The PDMS microchannel device was peeled off from the glass surface. The cells that remained on the glass surface were fixed with 4% paraformaldehyde and then subjected to blocking with 4% goat serum in washing solution (0.5% triton in 1×PBS). Primary antibodies including mouse anti-Vimentin (mIgG1, 1:100, Invitrogen), mouse anti-Met (mIgG1, 1:500, Cell Signaling Technology) and mouse anti-β3-Tubulin (mIgG2b, 1:500, Sigma-Aldrich) were prepared in blocking solution. Secondary antibodies including Goat anti-mIgG1 Dylight 594 (1:250, Jackson Immuno Research) and Goat anti-mIgG2b Alexa Fluor 488 (1:250, Jackson Immuno Research) were prepared in washing solution. Primary antibody incubation was conducted at 4° C. overnight and the secondary one at room temperature for 2 hours followed by DAPI staining for the nuclei for 20 minutes. The signals were observed under the fluorescent microscope and images in FIG. 7 were taken at 20×. For each protein of interest, the signal intensity of individual cell (n≥20 cells) was quantified using the Image J.

Quantification of immunohistochemistry staining in FIG. 5 affirmed Western Blot results, including significantly increased signals of Vimentin and decreased of β3-Tubulin and Met in the migrating cells compared to 2D/mixed population cells.

Example 6

Figure 10A:
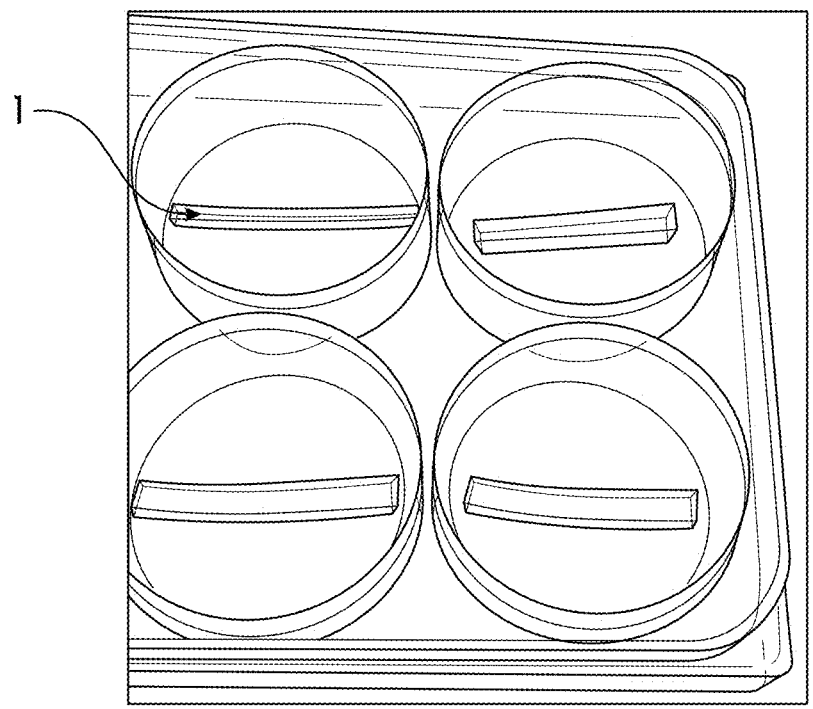
FIGS. 10A and 10B are photographs of one or more microchannel devices placed in wells on a plate.
Figure 10B:
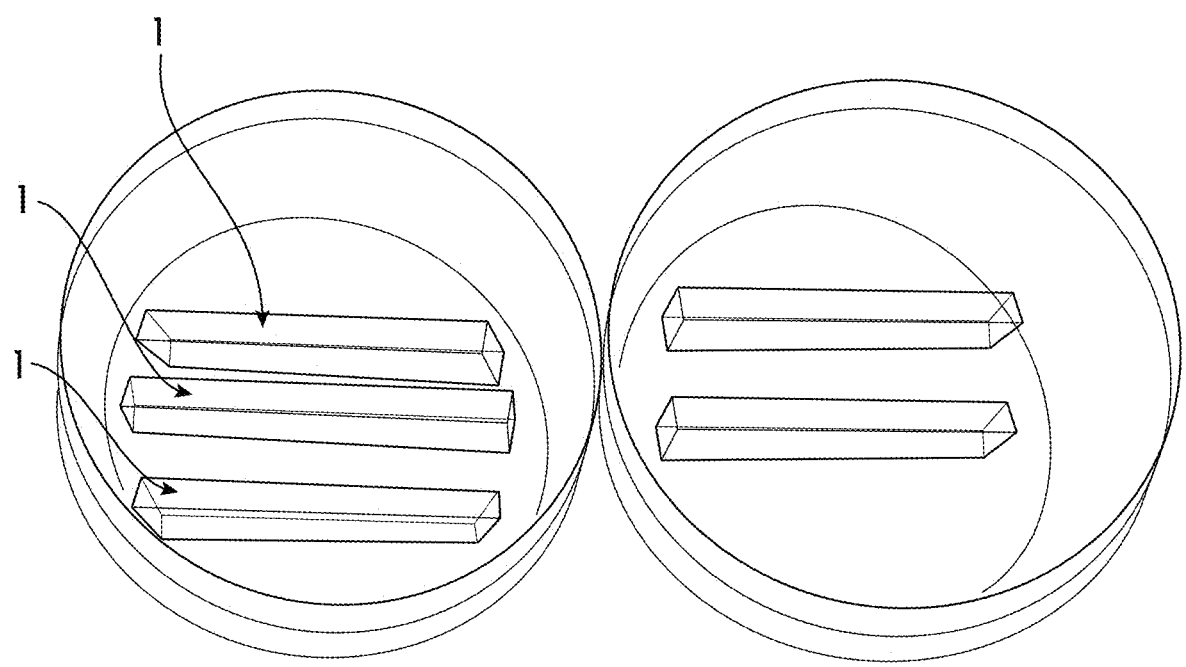
Figure 10C:
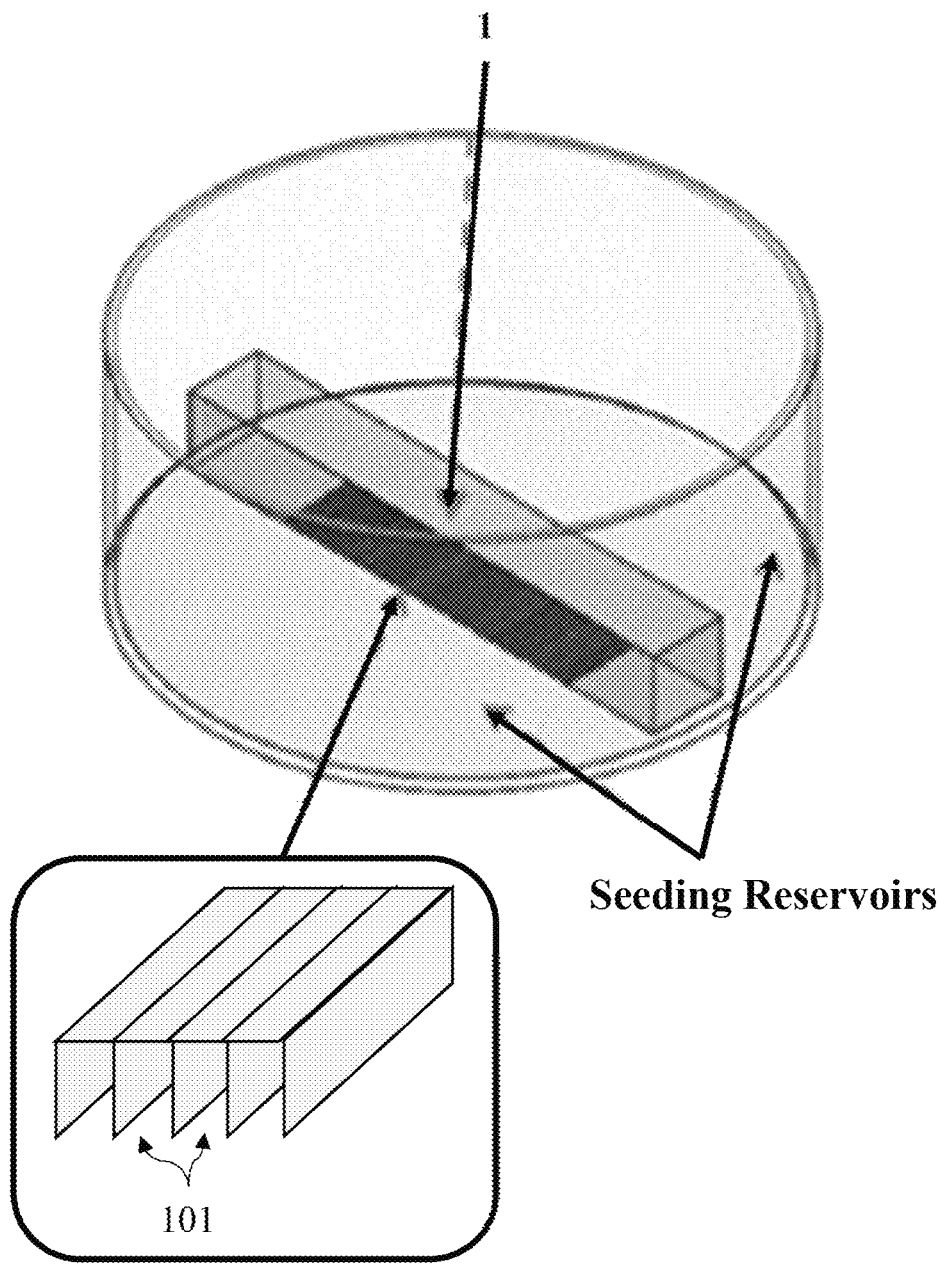
FIG. 10C is a perspective view of a microchannel device positioned in a well, with an expanded view of the microchannels of the device.

Isolation of a Migratory Cell Population in Multi-Well Plates and Protein Collection from the Isolated Migratory Cells microchannel arrays 1 as described in Example 1 were prepared and placed in 6, 12, 24, or 48-well plates, as shown for instance in FIGS. 10A-10C. In some cases, one microchannel array 1 was placed in each well (FIGS. 10A and 10C), although the invention is not limited to only one microchannel array 1, but in other instances, can have 2, 3, or more than 3 microchannel arrays 1 in each well. FIG. 10B shows a case where 3 microchannel arrays 1 were placed in each well.

As shown in FIG. 11, a mixed population of migratory and non-migratory cells were seeded to wells (i.e., seeding reservoirs) containing one or more microchannel arrays 1 (FIG. 10C), and the cells were allowed to culture for up to 7 days. During these culturing days, some cells migrate toward the microchannels (i.e., migratory cells) and other cells do not migrate toward the microchannels (i.e., non-migratory cells). 4-7 days after seeding the cells, the non-migratory 2D cells (i.e., cells are growing on the seeding reservoirs) were then cleaned from the well using Trypsin-EDTA solution and collected as non-migratory cell references. After confirming the absence of the non-migratory 2D cells on the seeding reservoirs under microscope observation, the microchannel array 1 was removed. The migratory cells were present in both the peeled microchannels 101 of microchannel array 1 and the area of the well-plate where microchannel array 1 was placed. The migratory cells in both the peeled microchannels 101 of microchannel array 1 and the area of the well-plate where microchannel array 1 was placed are collected for protein analysis using Western blot, as described in Example 4. Proteins (e.g., drug efflux proteins and cancer stem cell proteins) separately isolated and collected from the non-migratory 2D cells and the migrating cells were quantitatively identified and compared to determine the types of proteins related to cell migration, drug-resistance, and/or cancer stem cells.

Figure 11A:
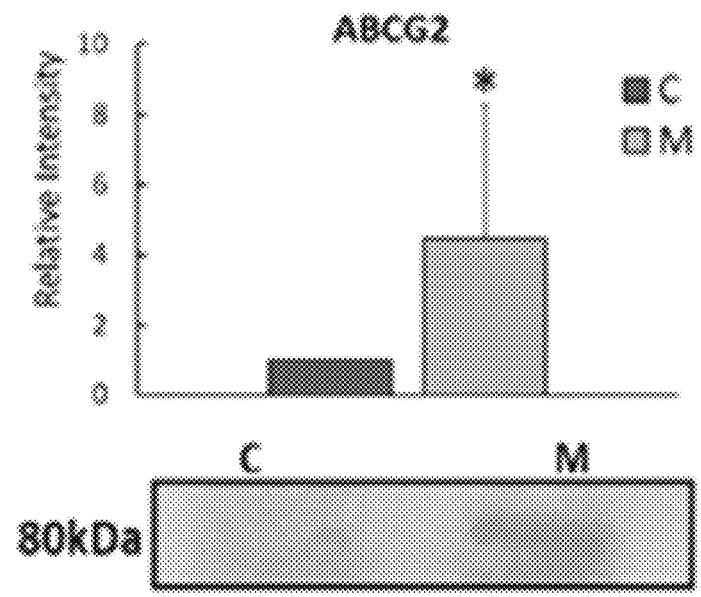
FIGS. 11A-11E show Western plot analysis based comparison of different drug efflux proteins in migratory cells isolated from a mixture of migratory cells and non-migratory cells of the same cell type using a microchannel device.
Figure 11B:
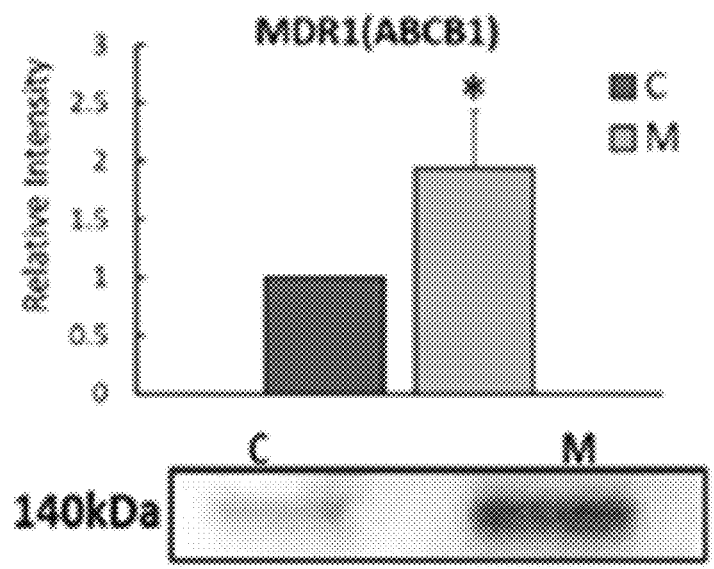
Figure 11C:
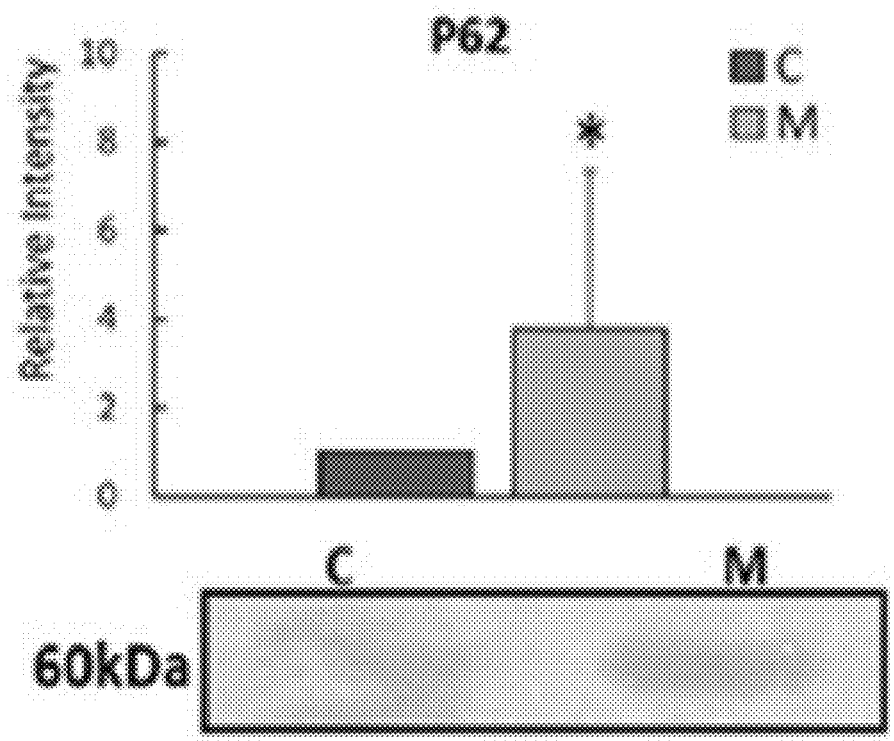
Figure 11D:
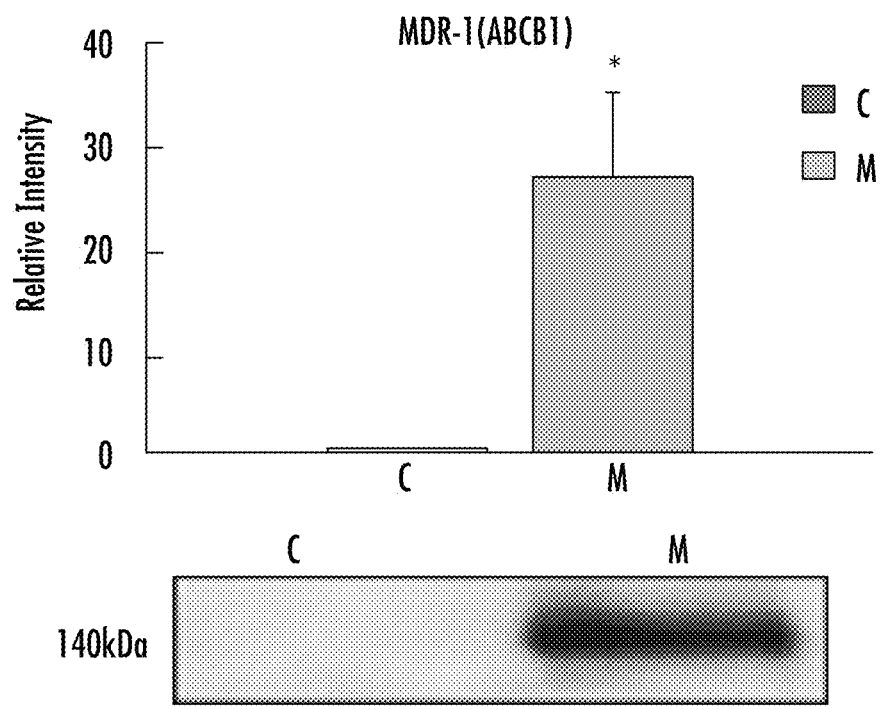
Figure 11E:
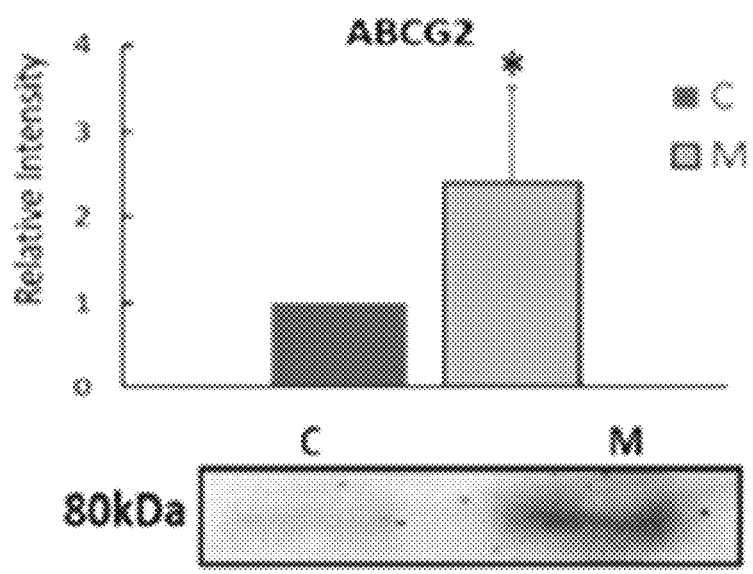

FIGS. 11A-11C show that various types of migrating cancer cells isolated from a mixed population of migratory and non-migratory cancer cells using the microchannel arrays 1 of Example 1 expressed significantly increased drug efflux proteins. FIGS. 11A-11C show a quantitative comparison of drug efflux proteins (ABCG2, MDR1 and P62) between G55 (Glioblastoma, brain cancer) migrating cells (indicated by M) and 2D non-migrating cells (indicated by C). All results were normalized by the total proteins. FIGS. 11D and 11E show a quantitative comparison of drug efflux proteins (ABCG2 and MDR-1) in MDA-MB-231 (malignant breast cancer) migrating cells (indicated by M) and 2D non-migrating cells (indicated by C).

Figure 12A:
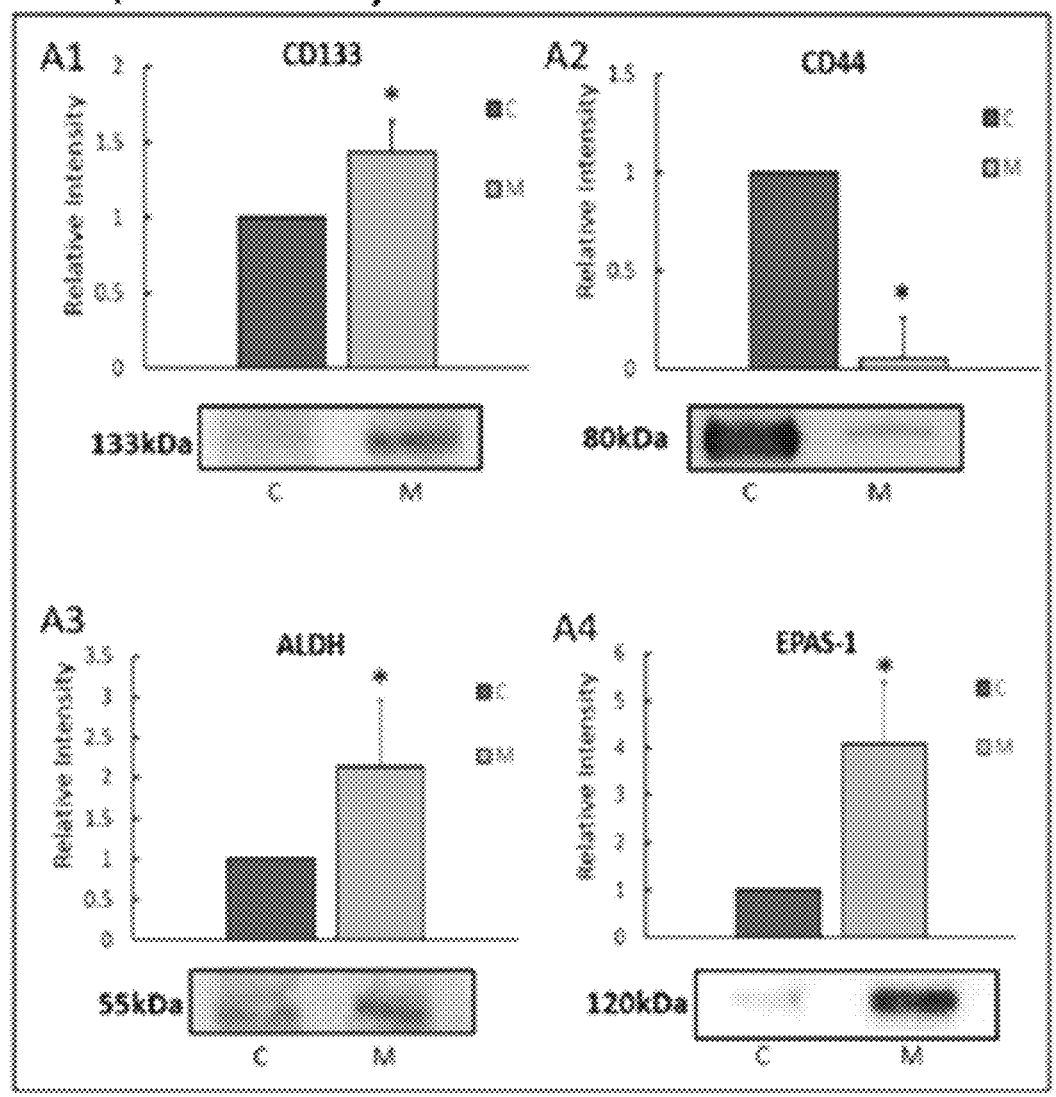
FIGS. 12A-12E show Western plot, analysis based comparison of different cancer stem cell related markers in migratory cells isolated from a mixture of migratory cells and non-migratory cells of the same cell type using a microchannel device.
Figure 12B:
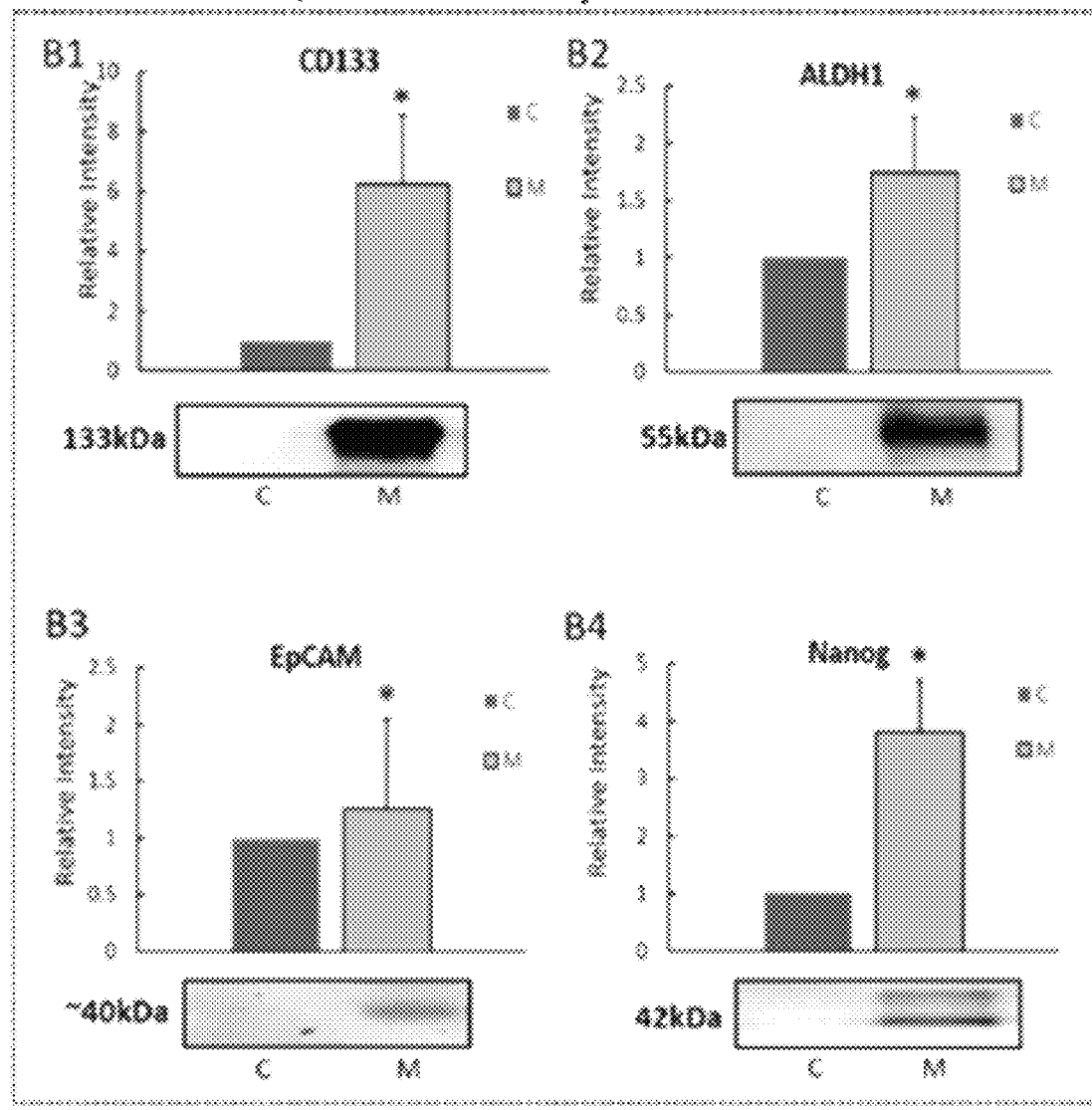
Figure 12C:
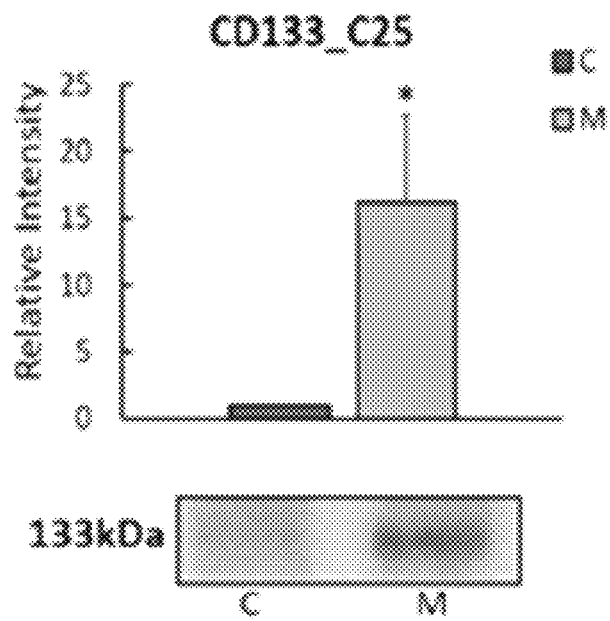
Figure 12D:
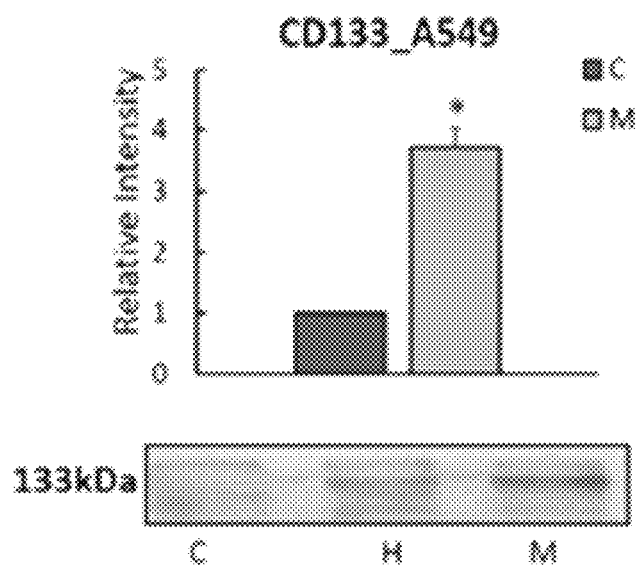
Figure 12E:
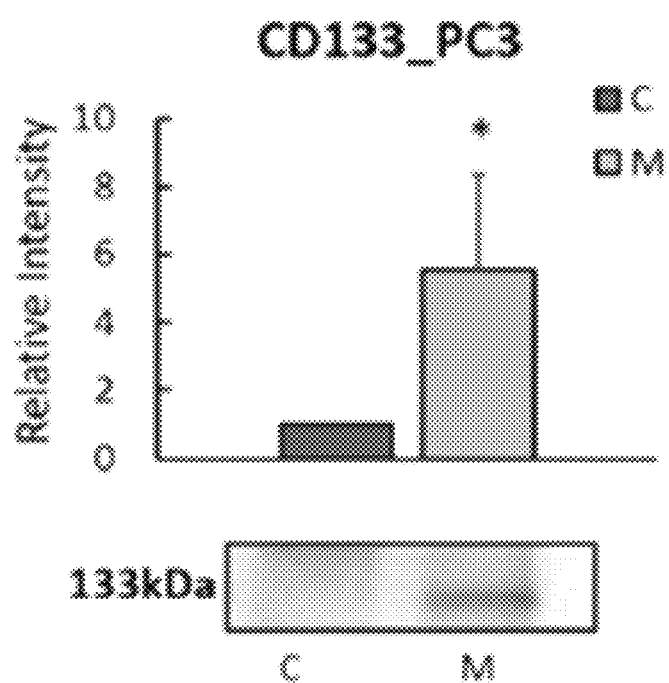

FIGS. 12A-12E show an increased expression of cancer stem cell related markers in migrating cancer cells isolated from a mixed population of migratory and non-migratory cancer cells using the microchannel device 1 of Example 1. The quantitative comparison of cancer stem cell related markers was performed using Western blot analyses between migrating (M) and 2D cultured (C) cancer cells. FIG. 12A shows Western blot analysis of G55 brain cancer cells. Cancer stem cells markers (i.e., CD133, ALDH, and EPAS-1) are significantly increased in the migrating brain cancer cells as compared to the non-migrating brain cancer cells. FIG. 12B shows Western blot analysis of MDA-MB-231 breast cancer cells. Similar to the brain cancer (FIG. 12A), cancer stem cells markers (i.e., CD133, ALDH, EpCAM and Nanog) are significantly increased in the migrating breast cancer cells as compared to the non-migrating breast cancer cells. FIGS. 12C-12E show increased expression of CD133 (i.e., cancer stem cell marker) in different types of migrating cancer cells, including C25 patient-derived GBM brain cancer cells, A549 lung cancer cell line, and PC3 prostate cancer cell line, respectively.

Accordingly, as shown in the Figures, the microchannel array 1 described herein can successfully isolate migratory cells from a mixed population of migratory and non-migratory cells, which is useful in identifying differentiated features (e.g., increased protein expression related to drug efflux and/or cancer stem cell) in migrating cells compared to those in non-migratory cells of the same cell type.

The invention claimed is:

1. A method of isolating a migratory cell population from a mixed population of migratory cells and non-migratory cells, the method comprising:
   placing the mixed population of migratory cells and non-migratory cells in contact with one or more microchannels;

commencing an incubation period to allow the migratory cells to migrate into the microchannels;

isolating the migratory cell population within the microchannels following the incubation period by attaching the migratory cells to the surface of the microchannels; and collecting the migratory cell population from the microchannels, wherein the one or more microchannels have an average size in a proliferation direction of the migratory cells that is less than a minimum proliferation space of the migratory cells along the proliferation direction, and wherein at least 500 migratory cells are isolatable within the microchannels at the same time by carrying out the steps as a single method of placing the mixed population of migratory cells and non-migratory cells in contact with one or more microchannels, commencing an incubation period to allow the migratory cells to migrate into the microchannels, isolating the migratory cell population within the microchannels following the incubation period by attaching the migratory cells to the surface of the microchannels, and collecting the migratory cell population from the microchannels only once.

2. The method of claim 1, wherein collecting the migratory cell population from the microchannels comprises extracting the migratory cell population from inside the microchannels.

3. The method of claim 1, wherein the proliferation direction is horizontal and the mixed population of cells are eukaryotic.

4. The method of claim 1, wherein the proliferation direction is vertical and the mixed population of cells are microbial.

5. The method of claim 1, wherein the microchannels free of a chemoattractant.

6. The method of claim 1, wherein the mixed population is placed in contact with a plurality of microchannels, and the plurality of microchannels comprise an array.

7. The method of claim 1, wherein the microchannels are positioned in a cell culture.

8. The method of claim 1, wherein the one or more microchannels have a cell receiving space with an average width of less than 10 μm that prevents cell proliferation within the microchannels.

9. The method of claim 1, wherein the microchannels comprise an opening on one end.

10. The method of claim 1, wherein each of the microchannels comprise an opening permeable to a liquid media via capillary action along the length of the microchannels.

11. The method of claim 1, wherein the microchannels have sidewalls that are impermeable to the migratory and non-migratory cells.

12. The method of claim 1, wherein placing the mixed population of migratory cells and non-migratory cells in contact with one or more microchannels comprises seeding the mixed population proximate an opening on an end of each of the microchannels.

13. The method of claim 1, wherein placing the mixed population of migratory cells and non-migratory cells in contact with one or more microchannels comprises placing the one or more microchannels adjacent to seeded cells of the mixed population.

14. The method of claim 7, wherein isolating the migratory cells within the microchannels comprises removing the microchannels from the cell culture.

15. The method of claim 1, wherein the average size in the proliferation direction of the migratory cells confines the migratory cells to a native size of the migratory cells.

16. The method of claim 15, wherein the native size of the migratory cells is the size of a whole cell or cell soma of the migratory cells while the migratory cells are in a non-dividing and non-differentiating state.

17. The method of claim 1, wherein the one or more microchannels have an average width of less than 10 μm.

* * * * *